United States Patent
Iikubo et al.

(10) Patent No.: US 11,564,468 B2
(45) Date of Patent: Jan. 31, 2023

(54) HAIR TREATMENT METHOD AND HAIR TREATMENT TOOL

(71) Applicant: Kao Corporation, Tokyo (JP)

(72) Inventors: Rina Iikubo, Sumida-ku (JP); Shuichiro Kobaru, Sumida-ku (JP); Yuki Kotaka, Sumida-ku (JP); Aguri Maruyama, Sumida-ku (JP); Kohsuke Kawaguchi, Sumida-ku (JP)

(73) Assignee: Kao Corporation, Tokyo (JP)

( * ) Notice: Subject to any disclaimer, the term of this patent is extended or adjusted under 35 U.S.C. 154(b) by 600 days.

(21) Appl. No.: 16/328,219

(22) PCT Filed: Jun. 22, 2017

(86) PCT No.: PCT/JP2017/022958
§ 371 (c)(1),
(2) Date: Feb. 25, 2019

(87) PCT Pub. No.: WO2018/037694
PCT Pub. Date: Mar. 1, 2018

(65) Prior Publication Data
US 2019/0208883 A1 Jul. 11, 2019

(30) Foreign Application Priority Data

Aug. 26, 2016 (JP) .............................. JP2016-166357
Aug. 26, 2016 (JP) .............................. JP2016-166358

(51) Int. Cl.
*A45D 19/00* (2006.01)
*A61K 8/02* (2006.01)
(Continued)

(52) U.S. Cl.
CPC ......... *A45D 19/018* (2021.01); *A45D 19/028* (2021.01); *A61K 8/02* (2013.01);
(Continued)

(58) Field of Classification Search
CPC .... A45D 19/00; A45D 19/02; A45D 19/0066; A45D 19/0075; A45D 19/0083;
(Continued)

(56) References Cited

U.S. PATENT DOCUMENTS 5,058,609 A 10/1991 Sandoz et al.
5,931,168 A 8/1999 Abercrombie et al.
(Continued)

FOREIGN PATENT DOCUMENTS

EP 1 958 532 A2 8/2008
EP 2 866 776 5/2015
(Continued)

OTHER PUBLICATIONS

Extended European Search Report dated Apr. 3, 2020 in corresponding European Patent Application No. 17843182.1, 7 pages
(Continued)

*Primary Examiner* — Rachel R Steitz
*Assistant Examiner* — Karim Asqiriba
(74) *Attorney, Agent, or Firm* — Oblon, McClelland, Maier & Neustadt, L.L.P.

(57) ABSTRACT

The invention relates to a hair treatment method for treating hair by using a hair treatment tool (1). The hair treatment tool (1) includes: a fiber structure member (5) that retains a hair cosmetic; and a liquid-impermeable sheet (3) to which the fiber structure member (5) is fixed. The fiber structure member (5) retains a hair cosmetic that includes a pigment and a film-forming resin, and is sealed in a packaging (2). The hair treatment method of the invention treats hair by: exposing a surface of the fiber structure member (5) of the hair treatment tool (1); and bringing the fiber structure member (5) into contact with hair, and in this state, moving the fiber structure member (5) in a direction of orientation of the hair.

8 Claims, 12 Drawing Sheets

(51) Int. Cl.
- *A61K 8/19* (2006.01)
- *A61Q 5/06* (2006.01)
- *A61K 8/898* (2006.01)
- *A61K 8/73* (2006.01)
- *A45D 19/02* (2006.01)
- *A61K 8/72* (2006.01)

(52) U.S. Cl.
CPC .................. *A61K 8/19* (2013.01); *A61K 8/72* (2013.01); *A61K 8/73* (2013.01); *A61K 8/898* (2013.01); *A61Q 5/06* (2013.01); *A61Q 5/065* (2013.01); *A45D 2200/1036* (2013.01)

(58) Field of Classification Search
CPC ............ A45D 19/0033; A45D 19/0041; A45D 19/012; A45D 19/016; A45D 19/018; A45D 19/022; A45D 19/024; A45D 2200/1036; A61Q 5/06; A61Q 5/065; A61K 8/02; A61K 8/027; A61K 8/19; A61K 8/72; A61K 8/0208; A61K 2800/87
See application file for complete search history.

(56) References Cited

U.S. PATENT DOCUMENTS

| | | | |
|---|---|---|---|
| 6,326,069 B1* | 12/2001 | Barnett | B65D 75/5855 |
| | | | 428/35.7 |
| 6,446,795 B1* | 9/2002 | Allen | B65D 75/20 |
| | | | 15/104.93 |
| 2003/0219399 A1 | 11/2003 | Hammond et al. | |
| 2003/0233714 A1* | 12/2003 | Hammond | A61K 8/45 |
| | | | 8/405 |
| 2004/0068813 A1* | 4/2004 | Calvillo | B32B 7/04 |
| | | | 15/104.93 |
| 2008/0083418 A1 | 4/2008 | Glenn et al. | |
| 2008/0083420 A1* | 4/2008 | Glenn | A61Q 5/12 |
| | | | 132/208 |
| 2008/0087293 A1* | 4/2008 | Glenn | A61Q 5/065 |
| | | | 132/210 |
| 2008/0087294 A1 | 4/2008 | Glenn et al. | |
| 2008/0127429 A1 | 6/2008 | Brun et al. | |
| 2015/0217921 A1* | 8/2015 | On | B65D 75/5855 |
| | | | 206/460 |
| 2016/0051452 A1* | 2/2016 | Nishizawa | A45D 19/16 |
| | | | 424/70.13 |
| 2016/0235654 A1 | 8/2016 | Herrlein et al. | |

FOREIGN PATENT DOCUMENTS

| | | |
|---|---|---|
| JP | 56-45538 Y2 | 4/1981 |
| JP | 58-14375 U | 1/1983 |
| JP | 60-81853 U | 6/1985 |
| JP | 10-117836 A | 5/1998 |
| JP | 11-178630 A | 7/1999 |
| JP | 2000-7540 A | 1/2000 |
| JP | 2000-72634 A | 3/2000 |
| JP | 2001-211925 A | 8/2001 |
| JP | 2002-238659 A | 8/2002 |
| JP | 2003-310337 A | 11/2003 |
| JP | 2004-91032 A | 3/2004 |
| JP | 2004-519505 A | 7/2004 |
| JP | 2005-270549 A | 10/2005 |
| JP | 2008-063251 | 3/2008 |
| JP | 2008-106068 A | 5/2008 |
| JP | 2010-503507 A | 2/2010 |
| JP | 2010-505502 A | 2/2010 |
| JP | 2013-241718 A | 12/2013 |
| JP | 2014-47450 A | 3/2014 |
| JP | 2015-189729 A | 11/2015 |
| JP | 2015-193621 A | 11/2015 |
| JP | 2018-34892 A | 3/2018 |
| JP | 2018-65757 A | 4/2018 |
| KR | 10-2015-0004550 U | 12/2015 |
| WO | WO 93/10687 A1 | 6/1993 |
| WO | WO 00/32321 A1 | 6/2000 |
| WO | WO 2008/044198 A1 | 4/2008 |
| WO | WO 2014/001391 A1 | 1/2014 |

OTHER PUBLICATIONS

Hagura T. et al: "Cosmetic-Containing Sheet Useful for Applying Cosmetics to Body, Obtained by Impregnating Liquid Cosmetic Containing Polyhydric Alcohol on Surface of Sheet-Like Base Material Made of Nonwoven Fabric Containing Cellulose Filament", WPI / Thomson, XP002761094, vol. 2012, No. 47, Jul. 5, 2012, 2 pages.

International Search Report dated Aug. 8, 2017 in PCT/JP2017/022958 filed on Jun. 22, 2017.

* cited by examiner (a)

(b)

(a)

(b)

(c)

(d)

HAIR TREATMENT METHOD AND HAIR TREATMENT TOOL

TECHNICAL FIELD

The present invention relates to a hair treatment method and a hair treatment tool.

BACKGROUND ART

Currently existing hair dye agents for changing hair color include: permanent hair dye agents for coloring hair by causing a dye precursor to permeate into the hair and causing a chemical reaction within the hair; semi-permanent hair dye agents in which a dye is caused to directly permeate into the hair; and temporary hair colorants in which a pigment etc. is caused to adhere to the surface of the hair.

Such hair dye agents, and especially permanent hair dye agents, are relatively easy to use for full coloring, in which all the hair on one's head is dyed uniformly. It is, however, difficult to perform partial coloring, or touch-up, in which a portion of the hair is selectively dyed, and this task is difficult for an ordinary consumer who is not a hairdresser to perform on his/her own. Thus, there have been proposed various dedicated tools for allowing a user to perform partial coloring easily.

For example, Patent Literature 1 discloses a partial hair dyeing tool in which a water-absorbent sheet for impregnation with a chemical solution, such as a hair dye agent or a bleaching agent, is provided on the inner surface of a cover material that can be folded in two and that is formed so as to be openable and closable. With this partial hair dyeing tool, partial coloring is achieved by: combing out a portion of hair; sandwiching the combed-out hair strand by the partial hair dyeing tool; and leaving the tool in this state for a while to wait for the chemical solution to permeate into the hair.

Patent Literature 2 discloses a partial hair dyeing tool, in which a hair strand is sandwiched between: a first sheet including a liquid-absorbent sheet for impregnation with a dyeing agent or a bleaching agent, and a liquid-impermeable sheet serving as a cover material and having an adhesive layer on the surface; and a second sheet consisting of a sheet having the same structure as the first sheet, or consisting only of a liquid-impermeable sheet. With this partial hair dyeing tool, the hair is dyed by fixing the first and second sheets in tight contact with one another, and then peeling the sheets apart after hair dyeing is finished.

Patent Literature 3 discloses a hair dyeing tool wherein microcapsules in which a hair dye liquid is sealed are provided on a base sheet material, and, by breaking the microcapsules, the base sheet material is impregnated with the dye, to thereby allow dyeing of hair. According to Patent Literature 3, it is only necessary to fold the base sheet material and sandwich a hair strand therebetween, and also, the dye liquid permeates into the base sheet material and thus does not seep out to the fingertips, thus preventing soiling of the fingers, clothes, etc. during dyeing.

Patent Literature 4 discloses a hair treatment applicator system including an absorbent substrate having a specific pore radius, and a highly viscous hair treatment composition. In the disclosed method for applying the hair treatment composition: a hair strand is held by the absorbent substrate in a state where the absorbent substrate is folded along one of its dimensions, so that the inner surface can be wrapped around the hair strand while the user holds the hair treatment application system between the thumb and the index finger; and, with the user holding the hair strand with the other hand, the hair treatment composition is applied by swiping the hair treatment applicator system along the entire length of the hair strand.

Patent Literature 5 discloses a hand-held applicator including: a flat, pouch-like container containing content, such as a hair coloring agent or a hair bleaching agent; an outlet for dispensing the content by pressing the principal surfaces of the container; and flaps for spreading the content. Patent Literature 5 describes that, with this applicator, it is possible to prevent soiling of the user's hands by the content, and also spread the content even over a surface that is easily ripped.

CITATION LIST

Patent Literature

Patent Literature 1: JP H10-117836A
Patent Literature 2: JP 2005-270549A
Patent Literature 3: JP 2000-72634A
Patent Literature 4: WO2008/044198A1
Patent Literature 5: WO2000/032321A1

SUMMARY OF INVENTION

The invention relates to a hair treatment method for treating hair by using a hair treatment tool. The hair treatment tool includes: a fiber structure member; and a liquid-impermeable sheet to which the fiber structure member is fixed. The fiber structure member retains a hair cosmetic that includes a pigment and a film-forming resin. The fiber structure member is sealed in a packaging. The hair treatment method involves steps 1 and 2 below:

step 1: exposing a surface of the fiber structure member of the hair treatment tool; and step 2: bringing the fiber structure member, whose surface has been exposed in step 1, into contact with hair, and in this state, moving the fiber structure member in a direction of orientation of the hair.

The invention also relates to a hair treatment tool including: a fiber structure member; and a liquid-impermeable sheet to which the fiber structure member is fixed. The fiber structure member retains a hair cosmetic that includes a pigment and a film-forming resin. The fiber structure member is sealed in a packaging.

BRIEF DESCRIPTION OF DRAWINGS

FIG. 3 illustrates diagrams illustrating another embodiment of a hair treatment tool used for a hair treatment method of the invention, wherein FIG. 3(a) is a plan view illustrating a state where the tool has been opened and spread out, and FIG. 3(b) is a perspective view before the tool is opened.

FIG. 11 illustrates perspective views illustrating steps for manufacturing the hair treatment tool illustrated in FIG. 3, wherein FIG. 11(A) is a perspective view illustrating a liquid-impermeable sheet and a fiber structure member constituting the hair treatment tool illustrated in FIG. 3, FIG. 11(B) is a perspective view illustrating a state where the fiber structure member is placed and fixed onto the liquid-impermeable sheet, and FIG. 11(C) is a perspective view illustrating a state where the fiber structure member and the liquid-impermeable sheet of FIG. 11(B) are folded in two.

FIG. 12 illustrates plan views illustrating seal portions in the hair treatment tool illustrated in FIG. 3, wherein FIG. 12(A) illustrates fixing seal portions provided along the sides parallel to the tearing direction of the hair treatment tool, and FIG. 12(B) illustrates an opening seal portion provided along a side parallel to an intersecting direction.

DESCRIPTION OF EMBODIMENTS

In Patent Literatures 1 and 2, the dye precursor or the dyeing agent needs to sufficiently permeate into the hair in order to develop color sufficiently, which requires time to hold and fix the hair dyeing tool on the hair. Thus, these tools are insufficient in terms of performing the treatment easily in a short time.

In Patent Literature 3, the microcapsules need to be broken by pressing upon application. In cases where the capsules are not broken sufficiently, the amount of dye that can be transferred may be insufficient, which may result in insufficient color development or uneven hair coloring.

Patent Literature 4 applies a highly viscous hair dye agent, which may impart an unpleasant feel to the hair. Also, the hair dye agent needs to be rinsed off with a shampoo etc. after the treatment, thus being insufficient in terms of simplicity.

With the applicator disclosed in Patent Literature 5, at the time of applying, to the hair, the content dispensed from the container containing the content, it is difficult to apply the content uniformly to the hair, possibly giving rise to uneven coloring.

As described above, Patent Literatures 1 to 5 are not sufficiently satisfactory in terms of performing coloring easily in a short time uniformly, with no uneven coloring from the root to the tip, without impairing the feel of the hair.

Further, Patent Literatures 1 to 4 are for applying, to the hair, a hair dye that is relatively easy to handle, and thus, when the hair dye permeates into the hair, the hair dye effect lasts even after several times of shampooing. The hair dyeing tools disclosed in Patent Literatures 1 to 4 are thus not suitable for cases where a user wants to enjoy hair coloring for a single day and then remove the coloring by shampooing to change the hair color back to its original color.

There are temporary hair colorants employing pigments, instead of dyes, for enjoying single-day coloring. Because of pigment dispersion, however, such temporary hair colorants developed thus far have limitations in terms of liquid property adjustment, such as viscosity, and the choice of containers. There has yet to be developed a tool that an ordinary consumer can easily use for applying a temporary colorant.

The invention provides a hair treatment tool, and a hair treatment method employing the same, capable of overcoming the aforementioned issues of conventional art.

A hair treatment tool of the invention is described below according to preferred embodiments thereof with reference to the drawings.

Figure 1:
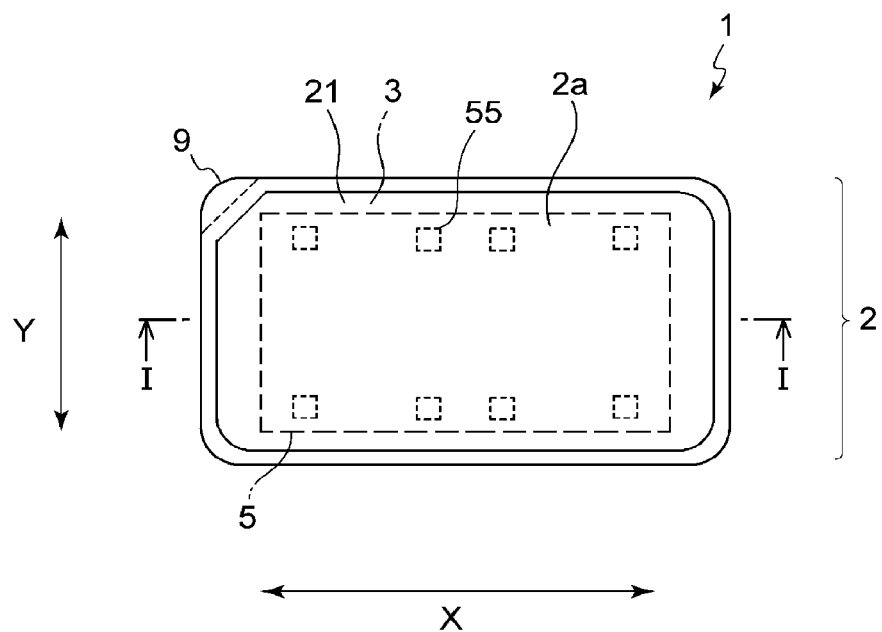
FIG. 1 is a plan view illustrating an embodiment of a hair treatment tool used for a hair treatment method of the invention.
Figure 2:
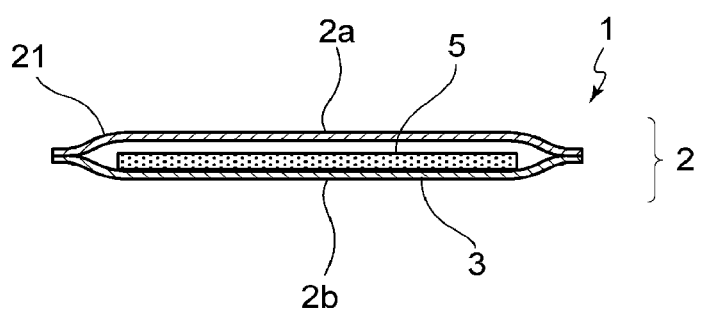
FIG. 2 is a cross-sectional view taken along line I-I of the treatment tool of FIG. 1.

FIGS. 1 and 2 illustrate a hair treatment tool (referred to hereinafter also as "hair treatment tool 1") which is an embodiment of a hair treatment tool used for a hair treatment method of the invention.

The hair treatment tool 1 includes: a fiber structure member 5 that retains a hair cosmetic; and a liquid-impermeable sheet 3 (referred to hereinafter also as "sheet 3") to which the fiber structure member 5 is fixed. The fiber structure member 5 is sealed in a packaging 2.

Figure 3:
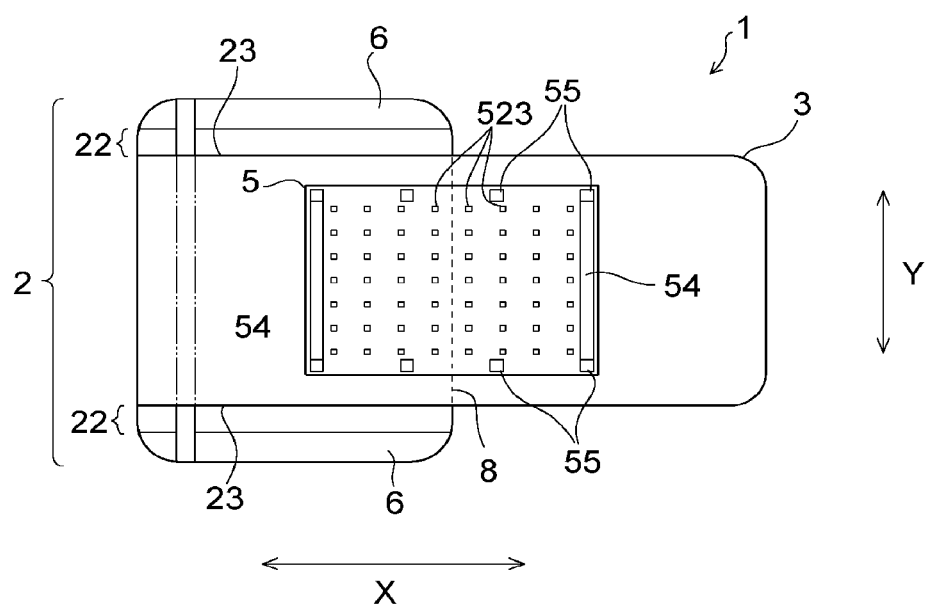
Figure 3:
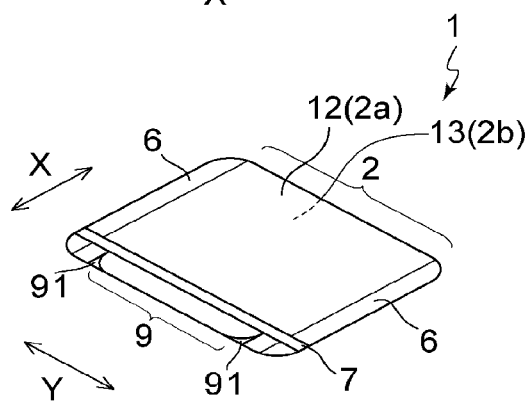

The packaging 2 can have any discretionary packaging form, so long as it can seal the fiber structure member 5. For example, in the hair treatment tool 1 of the invention, the fiber structure member 5 and the liquid-impermeable sheet 3 to which the fiber structure member 5 is fixed may be sealed inside a packaging 2 constituted by a separate sheet. Alternatively, as illustrated in FIG. 1, the fiber structure member 5 may be sandwiched between two separate sheets 21 and 3, and the four sides thereof may be joined to form the packaging 2. Alternatively, as illustrated in FIG. 3, the fiber structure member 5 may be sandwiched between a single sheet 3 folded in two, and the three sides of the bi-folded sheet may be joined to form a bag-shaped packaging 2. By sealing the fiber structure member by the packaging, it is possible to prevent leakage of the hair cosmetic, and in cases where the hair cosmetic includes a solvent, it is possible to effectively prevent seepage or volatilization of the solvent and also maintain the applicability of the hair cosmetic.

From the viewpoint of preventing the hands from getting soiled at the time of taking out the liquid-impermeable sheet 3 to which the fiber structure member 5 is fixed and also reducing waste, the entirety or a portion of the packaging 2 may be formed by the liquid-impermeable sheet 3 to which the fiber structure member 5 is fixed. More specifically, the packaging 2 illustrated in FIGS. 1 and 2 includes a sheet 21 forming an upper surface 2*a* and a sheet 3 forming a lower surface 2*b*, wherein the fiber structure member 5 is layered on the sheet 3 forming the lower surface 2*b*, and the sheet 3 constitutes the liquid-impermeable sheet 3 partially bonded with the fiber structure member 5. The packaging 2 illustrated in FIG. 3 is formed by folding the liquid-impermeable sheet 3 in two and joining predetermined sections of the sheet.

As described above, the packaging 2 can be formed by joining one or a plurality of sheets. To form the packaging 2, various known joining methods may be used, such as ultrasonic sealing, heat sealing, high-frequency sealing, or an adhesive. In cases where the hair cosmetic included in the fiber structure member 5 contains a large amount of organic solvent, it is preferable to use a joining method other than an adhesive, such as ultrasonic sealing, heat sealing, or high-frequency sealing.

Depending on the properties of the hair cosmetic, the packaging 2 may be made by using a discretionary material that does not let the hair cosmetic pass through. For example, it is possible to choose a sheet made of a material such as an aluminum foil, a thermoplastic resin film, a nonwoven fabric, or paper, or a sheet made by layering two or more of the above.

In cases where the hair cosmetic is a liquid, a liquid-impermeable sheet is chosen. The type of material used for the liquid-impermeable sheet is not particularly limited, so long as it is liquid-impermeable and flexible to some extent; for example, it is possible to use a thermoplastic resin film, or a laminate made by layering a metal thin film, such as aluminum, onto the film.

In cases where the hair cosmetic includes a volatile substance, it is possible to use a sheet material that does not let the volatile substance pass through. More specifically, the sheet material is preferably liquid-impermeable, and in addition to being liquid-impermeable, the sheet is preferably impermeable to water vapor and ethanol that have volatilized from the hair cosmetic. By using a sheet material having such properties, it is possible to effectively prevent seepage or volatilization of the hair cosmetic from the fiber structure member 5 inside the packaging 2 in cases where the hair cosmetic is in the form of a liquid or cream. Examples of sheet materials having such properties include aluminum-evaporated thermoplastic resin films and films including aluminum between thermoplastic resin films.

The liquid-impermeable sheet 3 is not particularly limited in type, so long as it is liquid-impermeable and flexible to some extent; for example, it is possible to use a thermoplastic resin film, or a laminate made by layering a metal thin film, such as aluminum, onto the film. In cases where the packaging 2 is formed by a portion or the entirety of the liquid-impermeable sheet 3, the aforementioned discretionary material may be used also for the liquid-impermeable sheet 3.

In cases where the packaging 2 is constituted by a plurality of sheets as illustrated in FIG. 1, different sheet materials may be used for the respective sheets. Further, as illustrated in FIG. 3, in cases where the packaging 2 is constituted by a first surface 2a and a second surface 2b, different sheet materials may be used for the sheets in the respective portions.

The packaging 2 preferably includes an opening means for exposing the fiber structure member 5 sealed inside the packaging. More specifically, the packaging 2 of the hair treatment tool 1 illustrated in FIG. 1 includes, in at least one of the four corners, a tab portion 9 where the sheet 21 forming the upper surface 2a and the sheet 3 forming the lower surface 2b are not joined together. By employing the tab portion 9 as a starting point, the sheet 21 forming the upper surface 2a is pulled in the direction of the diagonal of the packaging 2, and thereby, the entire sheet 21 can be peeled from the sheet 3. In this way, the fiber structure member 5 sealed in the packaging 2 is exposed.

In cases where the entirety or a portion of the packaging 2 is formed of the liquid-impermeable sheet 3, it is preferable that the liquid-impermeable sheet 3 includes an opening means, such as notches 91, serving as tear starting points. The packaging 2 of the hair treatment tool 1 illustrated in FIG. 3 is formed of the liquid-impermeable sheet 3, and, includes, as opening means, a tab portion 9 and notches 91, 91 that are cut along the tearing direction (the lateral direction X in FIG. 3(b)) at both ends of the tab portion 9, as illustrated in FIG. 3(b). In the packaging 2 of the hair treatment tool 1 illustrated in FIG. 3, pulling the tab portion 9 provided with the notches 91 in the tearing direction causes the liquid-impermeable sheet to be torn, and thereby, the sealed fiber structure member 5 can be exposed. This opening method is described further below.

Preferably, the liquid-impermeable sheet 3 has tearability, and more preferably, has tear rectilinearity. "Tear rectilinearity" refers to a property or structure that is easily torn rectilinearly in a specific direction. Examples of sheets having tear rectilinearity include: the aforementioned sheet provided with notches 91 at sections where tearing is started; a sheet having a cut line, such as a half-cut line, that does not penetrate the sheet in the thickness direction and that is provided rectilinearly along a specific direction; and a film material in which a polymer is oriented so that it tears easily in a specific direction by stretching.

From the viewpoint of preventing the adhesion of the hair cosmetic to the hands and reducing waste (unwanted parts), it is preferable that a portion of the liquid-impermeable sheet material constituting the packaging 2 that seals the fiber structure member 5 is the liquid-impermeable sheet 3 to which the fiber structure member 5 is fixed in a state of use, and it is preferable that the entire liquid-impermeable sheet material constituting the packaging 2 that seals the fiber structure member 5 is the liquid-impermeable sheet 3 to which the fiber structure member 5 is fixed in a state of use, as in the hair treatment tool 1 of the embodiment illustrated in FIG. 3.

The fiber structure member 5 retains the hair cosmetic, and is sealed in the packaging 2. The fiber structure member 5 inside the packaging 2 is either not folded (see FIG. 1), or is sealed by being folded in a predetermined shape (see FIG. 3). From the viewpoint of improving portability of the hair treatment tool 1 and improving usability upon applying the hair cosmetic by sandwiching the hair with the fiber structure member 5, it is preferable that the fiber structure member 5 is sealed in a folded state in the packaging 2. The fiber structure member 5 may be folded in two as illustrated in FIG. 3, or may be folded a plurality of times in three or more.

For the fiber structure member 5, it is possible to use a discretionary material capable of retaining a hair cosmetic. For example, it is possible to preferably use a fiber sheet made of fiber material, such as a nonwoven fabric, a knitted sheet, or paper. Examples of nonwoven fabric usable as the fiber structure member 5 include nonwoven fabrics made by various manufacturing methods, such as spun-laced nonwoven fabrics, melt-blown nonwoven fabrics, needle-punched nonwoven fabrics, and air-through nonwoven fabrics. Examples of paper that may be used include paper obtained by dry sheet-forming methods, wet sheet-forming methods, or the like. The fiber structure member 5, which may be made for example of a nonwoven fabric or paper, preferably includes cellulosic fiber as its constituent fiber, from the viewpoint of retainability of the hair cosmetic particularly in cases where the hair cosmetic is a liquid. Further, from the viewpoint of improving the strength of the nonwoven fabric, preventing fuzzing etc. upon application to the hair, and suppressing the adhesion of fibers to the hair, it is preferable that the fiber structure member also includes a synthetic fiber, such as thermoplastic resin fiber, in addition to cellulosic fiber. Examples of the thermoplastic resin fiber include polyolefins such as polypropylene and polyethylene, polyesters such as polyethylene terephthalate, and polyamides such as nylon. The synthetic fiber may be a conjugate fiber made of a plurality of types of resin components, such as a core-sheath fiber or a side-by-side fiber. A thermosetting fiber may also be used instead of, or in addition to, the thermoplastic resin fiber.

One type of the aforementioned fiber may be used singly, or two or more types may be used in combination. It is preferable to choose an appropriate fiber structure member 5 depending on the properties of the hair cosmetic, and the aforementioned fiber sheet, such as nonwoven fabric, is preferably used in cases where the hair cosmetic is in the form of a liquid, cream, powder, or the like.

From the viewpoint of bringing the fiber structure member 5 into contact with the hair, it is preferable that the planar-view shape of the fiber structure member when spread open is rectangular as illustrated in FIG. 1 and FIG. 3(a), but it may be formed in a discretionary shape other than rectangular; for example, it may be circular, elliptic, heart-shaped, or polygonal, such as triangular, square, or pentagonal. The fiber structure member 5 of the present embodiments is rectangular with the long sides along the lateral direction X in a planar view, but it may be rectangular with the short sides in the lateral direction X. Further, the packaging 2 of the present embodiments is rectangular with its corners rounded, but the corners do not have to be rounded.

The fiber structure member 5 may be constituted by a single fiber sheet, but preferably, it is a multi-ply sheet made by layering a plurality of sheets.

From the viewpoint of ensuring the amount of retention of the hair cosmetic, further improving operability upon hair treatment, and improving portability, the thickness of the fiber structure member 5 made of fiber material is preferably 0.4 mm or greater, more preferably 1.0 mm or greater, even more preferably 1.5 mm or greater, and preferably 15 mm or less, more preferably 10 mm or less, even more preferably 5 mm or less. Herein, the thickness of the fiber structure member is the thickness measured under a load of 0.8 cN/cm$^2$, and is measured with a digital indicator. In cases where the fiber structure member is made by layering a plurality of sheets, the thickness refers to the thickness of the layered sheets.

From the same viewpoint, the basis weight of the fiber structure member 5 made of fiber material is preferably 10 g/m$^2$ or greater, more preferably 20 g/m$^2$ or greater, and preferably 300 g/m$^2$ or less, more preferably 200 g/m$^2$ or less. In cases where the fiber structure member is made by layering a plurality of sheets, the basis weight refers to the basis weight of the layered sheets.

The fiber structure member 5 preferably includes cellulosic fiber. Including cellulosic fiber makes it easy to ensure the amount of retention of the hair cosmetic.

Examples of usable cellulosic fibers include hydrophilic fibers such as natural fibers or regenerated fibers. Examples of natural cellulosic fibers include pulp fiber and cotton fiber. Examples of regenerated cellulosic fibers include rayon, cupra rayon, lyocell, and Tencel. One type of cellulosic fiber may be used singly, or two or more types may be used in combination.

From the viewpoint of achieving the aforementioned effect of operability more reliably, it is preferable that at least the surface side of the fiber structure member 5 includes preferably 5 mass % or greater of cellulosic fiber. Herein, the "surface of the fiber structure member 5" is the surface that comes in to contact with the hair when treating the hair by using the hair treatment tool 1; in cases where the fiber structure member 5 is flat as in the fiber structure member 5 of the present embodiment, the "surface" is the surface, of the two surfaces present in the thickness direction, that comes in to contact with the hair during use of the hair treatment tool.

Examples of configurations in which at least the surface side includes 5 mass % or greater of cellulosic fiber include the following: the constituent fibers of the fiber structure member 5 are uniform in the thickness direction and the entire fiber structure member includes 5 mass % or greater of cellulosic fiber; and the fiber structure member has a layered structure made by layering a plurality of layers, and the constituent fibers in the uppermost layer (referred to hereinafter also as "surface layer") constituting the surface that comes in to contact with the hair include 5 mass % or greater of cellulosic fiber.

From the viewpoint of improving the feel upon use and applicability, it is preferable that at least the surface side of the fiber structure member 5 includes preferably 5 mass % or greater, more preferably 10 mass % or greater, of cellulosic fiber. From the viewpoint of uniform applicability of the hair cosmetic, it is preferable that at least the surface side of the fiber structure member 5 includes preferably 60 mass % or less, more preferably 50 mass % or less, of cellulosic fiber. From the viewpoint of achieving both the effects of the retainability and uniform applicability of the hair cosmetic, it is preferable that at least the surface side includes preferably from 5 to 60 mass %, more preferably from 10 to 50 mass %, of cellulosic fiber. Particularly, in cases where the hair cosmetic includes a relatively large amount of organic solvent, from the viewpoint of achieving liquid absorptivity and sustained releasability of the hair cosmetic in a balanced manner and allowing the hair cosmetic to be applied to the hair thinly and uniformly, it is preferable that the content of cellulosic fiber, i.e., hydrophilic fiber, is within the aforementioned range, and the content of hydrophobic fiber, such as thermoplastic resin fiber or thermosetting fiber, is preferably 40 mass % or greater, more preferably 50 mass % or greater, and preferably 95 mass % or less, more preferably 90 mass % or less.

On the other hand, from the viewpoint of retainability of the hair cosmetic, it is preferable that at least the surface side of the fiber structure member 5 includes preferably more than 60 mass %, more preferably 65 mass % or greater, of cellulosic fiber. From the viewpoint of improving temporal stability of the hair cosmetic, it is preferable that at least the surface side of the fiber structure member 5 includes preferably 90 mass % or less, more preferably 80 mass % or less, of cellulosic fiber. From the viewpoint of achieving both the effects of retainability and temporal stability of the hair cosmetic, it is preferable that at least the surface side of the fiber structure member 5 includes preferably more than 60 mass % to 90 mass % or less, more preferably from 65 to 80 mass %, of cellulosic fiber.

Figure 4:
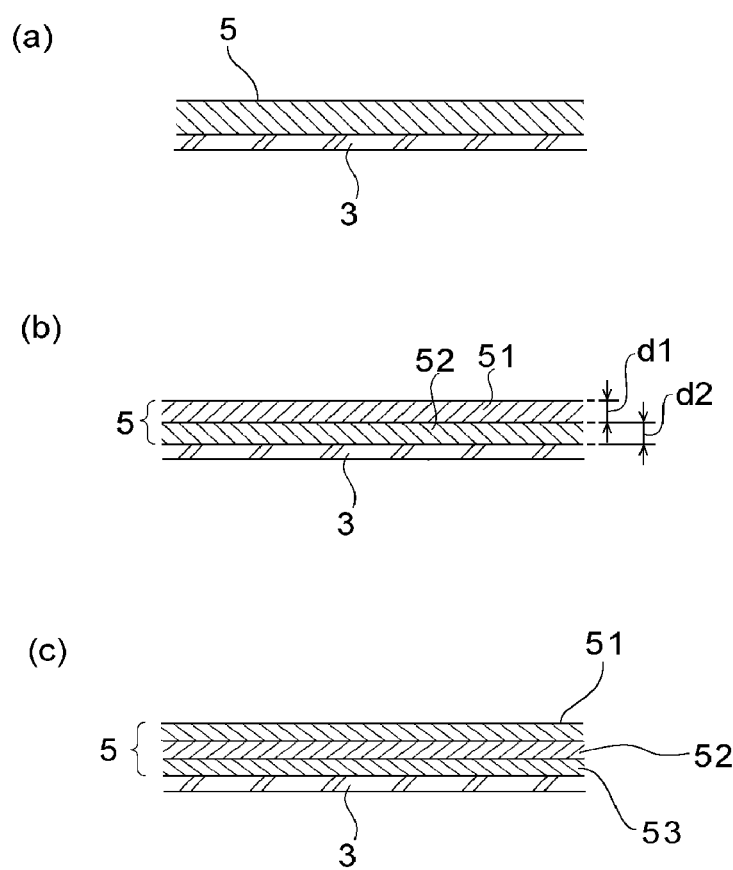
FIG. 4 illustrates cross-sectional views illustrating variations of cross-sectional structures of fiber structure members.

As illustrated in FIG. 4(a), the fiber structure member 5 may be constituted by a single-layer fiber sheet, but preferably, the fiber structure member has a layered structure including a plurality of layers, as illustrated in FIGS. 4(b) and 4(c). This is because a layered structure further improves the impregnation retainability of the hair cosmetic.

A "layered structure" encompasses a state in which a plurality of fiber sheets are layered, as well as a state in which a single fiber sheet is folded at least once to form multiple layers. In a layered structure, a plurality of layers having the same fiber constitution may be layered, or a plurality of layers having different fiber constitutions may be layered.

Further, in cases where the fiber structure member 5 has a layered structure, the number of sheets forming the layers is not limited, but is preferably 1 or greater, more preferably 3 or greater, and preferably 15 or less, more preferably 10 or less.

As illustrated in FIG. 4(b), preferably, the fiber structure member 5 has a layered structure including: an application layer 51 including a surface layer constituting the surface that contacts the hair; and a lower layer 52 arranged more toward the liquid-impermeable sheet 3 side than the application layer 51. This is because it is possible to apply the hair cosmetic to the hair more uniformly while sufficiently maintaining the amount of application of the hair cosmetic to the hair during hair treatment with the hair treatment tool 1, and thus the pigment is effectively transferred so as to develop color uniformly and sufficiently on the hair. Particularly, in cases where the hair cosmetic includes a relatively large amount of organic solvent and the liquid viscosity is relatively low as described further below, the aforementioned structure is preferable from the viewpoint of balancing retainability and dischargibility of the hair cosmetic. Herein, the application layer 51 and the lower layer 52 are distinguished from one another in terms that their hair cosmetic impregnation rates are different. Herein, "impregnation rate" refers to the rate (percentage; %) of the mass of the application layer 51 or lower layer 52 after impregnation to the mass thereof before impregnation. For example, in the fiber structure member 5, the impregnation rate of the lower layer 52 may be higher than that of the application layer 51, or the impregnation rate of the lower layer 52 may be lower than that of the application layer 51.

For example, the impregnation rate of the hair cosmetic can be adjusted by the content by percentage of cellulosic fiber in all constituent fibers in each layer. In this case, the content by percentage of cellulosic fiber in all constituent fibers of the application layer 51 is different from the content by percentage of cellulosic fiber in all constituent fibers of the lower layer 52.

From the viewpoint of applying the hair cosmetic more uniformly and improving color development by the hair cosmetic, it is preferable to use a nonwoven fabric in which the impregnation rate of the hair cosmetic is higher in the lower layer 52 than in the application layer 51. To achieve this configuration, for example, the content by percentage of cellulosic fiber in all constituent fibers of the application layer 51 may be made lower than the content by percentage of cellulosic fiber in all constituent fibers of the lower layer 52. In this case, it is preferable that the content by percentage of cellulosic fiber in the lower layer 52 with respect to the mass of all constituent fibers in the lower layer 52 is preferably 60 mass % or greater, and preferably 95 mass % or less, more preferably 90 mass % or less, and preferably from 60 to 95 mass %, more preferably from 60 to 90 mass %.

On the other hand, from the viewpoint of improving temporal stability of the hair cosmetic in the fiber structure member, it is preferable to use a nonwoven fabric in which the impregnation rate is higher in the application layer 51 than in the lower layer 52. To achieve this configuration, for example, the content by percentage of cellulosic fiber in all constituent fibers of the application layer 51 may be made higher than the content by percentage of cellulosic fiber in all constituent fibers of the lower layer 52. In this case, it is preferable that the content by percentage of cellulosic fiber in the application layer 51 with respect to the mass of all constituent fibers in the application layer 51 is preferably 60 mass % or greater, more preferably greater than 60 mass %, and preferably 95 mass % or less, more preferably 90 mass % or less, and preferably from 60 to 95 mass %, more preferably greater than 60 mass % to 95 mass % or less, even more preferably from 60 to 90 mass %.

In the present invention, "temporal stability" means that, even if there is a difference in time from when the hair cosmetic-retaining fiber structure member is sealed in the packaging until when the hair treatment tool is opened and used—for example, even if the tool is opened and used after one week from sealing—the hair cosmetic can be discharged moderately from the fiber structure member during use, and can treat the hair uniformly.

Regardless of the impregnation rate of the application layer 51 or the impregnation rate of the lower layer 52, it is preferable that the content by percentage of cellulosic fiber in the application layer 51 is within the same range as the content by percentage of cellulosic fiber at the surface (the surface layer) of the fiber structure member 5 described above.

Each of the application layer 51 and the lower layer 52 may be constituted by a single layer, or by a layered structure formed by layering a plurality of sheets. Stated differently, the fiber structure member 5 including the application layer 51 and the lower layer 52 may be constituted by any of the following: a single-layer application layer 51 and a single-layer lower layer 52; a single-layer application layer 51 and a layered-structure lower layer 52; a layered-structure application layer 51 and a single-layer lower layer 52; or a layered-structure application layer 51 and a layered-structure lower layer 52. In cases where the application layer 51 is a single layer, the application layer 51 constitutes the surface layer. For example, a layered-structure application layer 51 may include a plurality of layers each having the same content by percentage of cellulosic fiber as the surface layer. For example, a layered-structure lower layer 52 may include a plurality of layers, each having a content by percentage of cellulosic fiber higher than that of the application layer, arranged more toward the liquid-impermeable sheet 3 side than the application layer. In cases where the application layer 51 or the lower layer 52 has a layered structure, it is preferable that the content by percentage of cellulosic fiber in each layer constituting the application layer 51 or the lower layer 52 is within the aforementioned range of the content by percentage of cellulosic fiber in the respective application layer 51 or lower layer 52. In cases where the application layer 51 has a layered structure, the impregnation rate of the hair cosmetic in each of the layers constituting the application layer 51 is the same. In the layered structure, for example, the impregnation rate of the hair cosmetic in each of the layers of the layered structure can be made the same by forming the layered structure by layering a plurality of sheets having the same content by percentage of cellulosic fiber. In cases where the lower layer 52 has a layered structure, the impregnation rate of the hair cosmetic in each of the layers constituting the lower layer 52 is the same. In cases where the fiber structure member 5 includes a plurality of layers (sheets) having the same impregnation rate, the fiber structure member 5 only includes the application layer 51, and no lower layer 52.

The impregnation rate of the hair cosmetic can be adjusted by the content by percentage of cellulosic fiber constituting each layer.

From the viewpoint of controlling sustained releasability of the hair cosmetic and uniformly applying the pigment in the hair cosmetic so as to develop color satisfactorily, for example, a layer 53 having a lower impregnation rate than the lower layer 52 may be provided more toward the liquid-impermeable sheet 3 side than the lower layer 52, as illustrated in FIG. 4(c).

The thickness d1 of the application layer 51 is preferably smaller than the thickness d2 of the lower layer 52. This is because the hair treatment tool 1 can be provided with sustained releasability, and the hair cosmetic can be applied more uniformly over the length direction of the hair.

From the viewpoint of achieving the aforementioned effects more reliably, the ratio (d2/d1) of the thickness d2 of the lower layer 52 to the thickness d1 of the application layer 51 is preferably 0.7 or greater, more preferably 0.9 or greater, more preferably 1.0 or greater, even more preferably 1.3 or greater, and preferably 15 or less, more preferably 10 or less, even more preferably 7.5 or less, and preferably from 0.7 to 15, more preferably from 0.9 to 15, more preferably from 1.0 to 10, even more preferably from 1.3 to 7.5.

From the same viewpoint, the thickness d1 of the application layer 51 is preferably 0.2 mm or greater, more preferably 0.6 mm or greater, and preferably 8 mm or less, more preferably 3 mm or less, and preferably from 0.2 to 8 mm, more preferably from 0.6 to 3 mm. From the same viewpoint, the thickness d2 of the lower layer is preferably 0.2 mm or greater, more preferably 0.4 mm or greater, and preferably 12 mm or less, more preferably 6 mm or less, and preferably from 0.2 to 12 mm, more preferably from 0.4 to 6 mm.

The fiber structure member 5 retains the hair cosmetic; the impregnation rate of the hair cosmetic in the fiber structure member 5 is preferably 200% or greater, more preferably 250% or greater, and preferably 1000% or less, more preferably 800% or less, and preferably from 200 to 1000%, more preferably from 250 to 800%. Herein, "impregnation rate" refers to the rate (percentage; %) of the mass of the fiber structure member 5 after impregnation to the mass of the fiber structure member 5 before impregnation.

Figure 7:
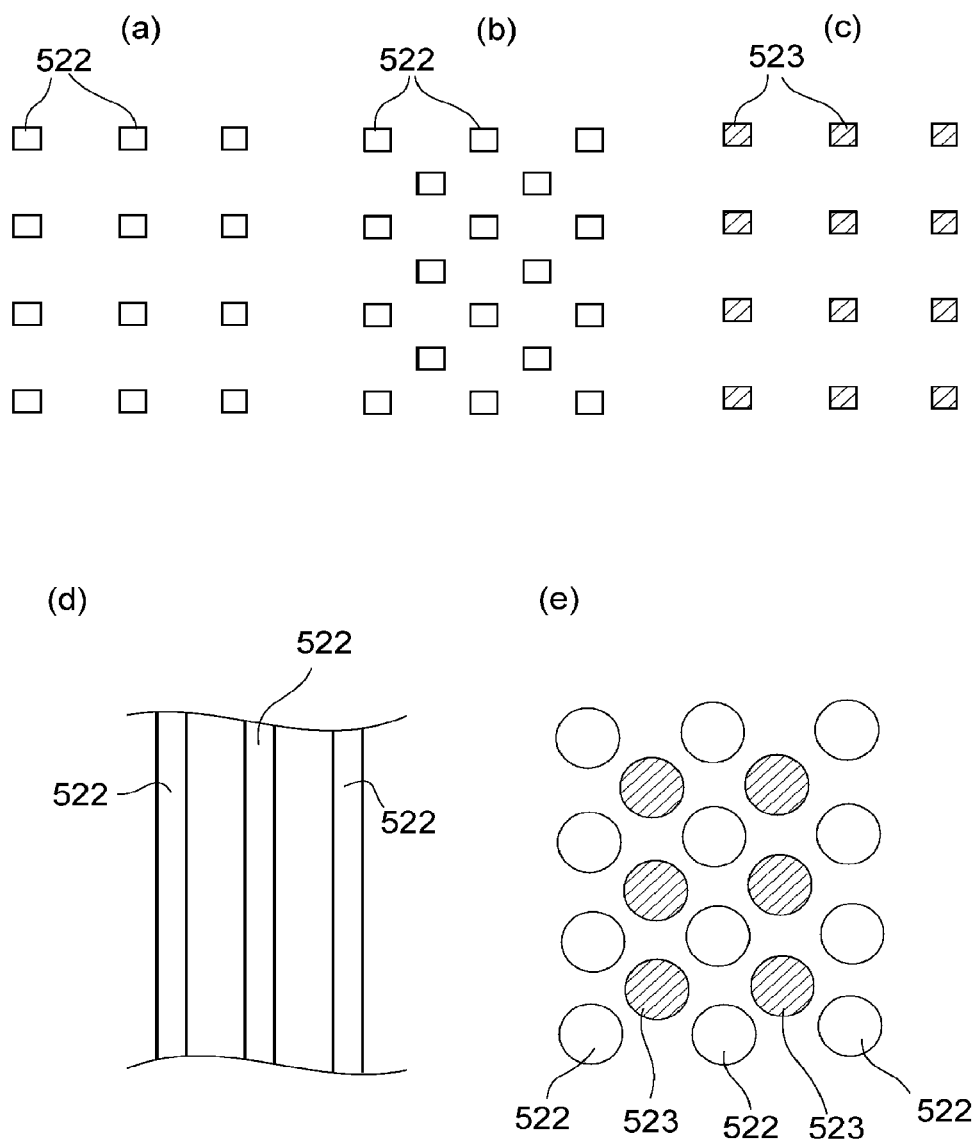
FIGS. 7(*a*) to (*e*) are diagrams illustrating examples of patterns of projections and depressions of fiber structure members according to the invention.

From the viewpoint of controlling sustained releasability of the hair cosmetic and uniformly applying the hair cosmetic with excellent color development, it is preferable that the fiber structure member 5 has, on one surface or both surfaces thereof, depressions, projections, or both. For example, projections, depressions, or both, may be dispersedly arranged in a scattered manner on one surface or both surfaces of the fiber structure member 5; or, projections, depressions, or both, may be formed in a plurality of rows in a manner extending in a specific direction within the plane of the fiber structure member. Specific examples include: configurations in which a plurality of projections 522 or depressions 523 are arranged in the lateral direction and the longitudinal direction (FIGS. 7(a) and 7(c)); configurations in which a plurality of projections 522 are arranged in a staggered pattern (FIG. 7(b)); configurations in which a plurality of continuous projections (ridges) are arranged in a single direction (FIG. 7(d)); and configurations in which a plurality of depression rows, each including a plurality of depressions arranged in a single direction, and a plurality of projection rows, each including a plurality of projections arranged similarly in a single direction, are arranged alternately (FIG. 7(e)).

Figure 8:
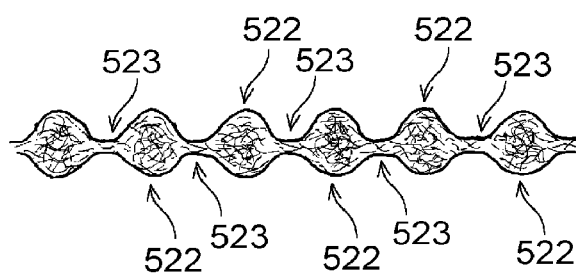
FIG. 8 is a cross-sectional view illustrating an embodiment of a fiber structure member according to the invention.

From the viewpoint of controlling dischargibility of the hair cosmetic composition and applying the hair cosmetic composition to the hair thinly and uniformly, an example of a fiber structure member 5 configured as above is a fiber structure member in which, in a planar view, the positions where the projections 522 are formed on one surface substantially match the positions where the projections 522 are formed on the other surface (see FIG. 8). More specifically, examples include sheets illustrated in FIGS. 2 to 4 of JP 2014-210767A.

The depressions and projections can be formed, for example, by: embossing; employing a meshed net having openings (holes) as disclosed in paragraph 0035 of JP 2014-108306A; or pressing the fiber structure member against a rotary roller having projections.

The fiber structure member 5 is fixed to the liquid-impermeable sheet 3. A portion, or the entirety, of the fiber structure member 5 may be fixed to the liquid-impermeable sheet 3. In cases where the fiber structure member 5 is sheet-like, the entire region of the fiber structure member 5 may be fixed to the liquid-impermeable sheet 3, but it is preferable that it is partially fixed to the liquid-impermeable sheet 3 at one or more sections on the surface opposite from the surface that comes into contact with the hair. More specifically, as illustrated in FIG. 1 and FIG. 3(a), the fiber structure member 5 may be fixed to the liquid-impermeable sheet 3 by a plurality of fixing parts 54 and 55 separated from one another in the lateral direction X and the longitudinal direction Y.

Note that, as illustrated in FIG. 1 and FIG. 3(a), the fiber structure member 5 in the respective embodiments includes, in a planar view, first sides constituting the long sides and parallel to one another and second sides constituting the short sides and parallel to one another, and, in relation to these sides, the hair treatment tool 1 in the respective embodiments has a lateral direction X parallel to the first sides, and a longitudinal direction Y orthogonal to the lateral direction X.

The fiber structure member 5 and the liquid-impermeable sheet 3 may be fixed together by known joining means such as an adhesive or fusion bonding. In cases where the hair cosmetic includes a relatively large amount of organic solvent, it is preferable that, in the hair treatment tool 1 of the respective embodiments, the fiber structure member 5 is fixed to the liquid-impermeable sheet 3 by means other than an adhesive, such as heat sealing, ultrasonic sealing, or high-frequency sealing, from the viewpoint of storage stability of the hair treatment tool itself and the prevention of intrusion of adhesive into the hair cosmetic (so-called contamination). If necessary, however, an adhesive may be used singly, or an adhesive and fusion bonding may be used in combination.

The liquid-impermeable sheet 3 and the fiber structure member 5 are fixed, and preferably, the fiber structure member 5 is fixed to one surface of the liquid-impermeable sheet 3. Upon hair treatment, a user of the hair treatment tool can hold the surface where the fiber structure member 5 is not fixed, and thus, the hair cosmetic can be prevented from adhering to the user's fingers and palm, for example.

Figure 6:
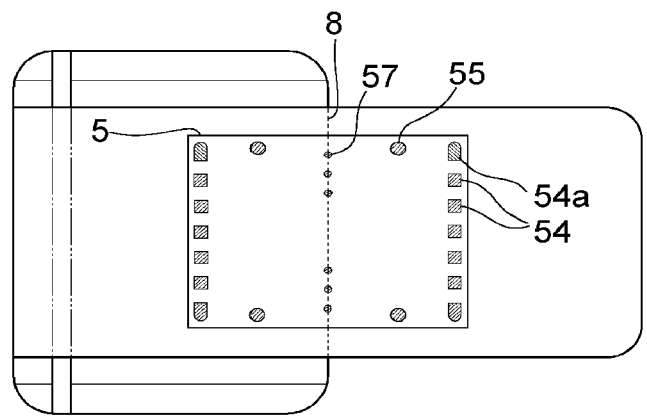
FIG. 6 is a plan view illustrating an example of a position for fixing a fiber structure member and a liquid-impermeable sheet according to the invention.

From the viewpoint of easy conformability of the fiber structure member 5 to the surface of the hair and further improvement of uniform applicability, it is preferable that the fiber structure member 5 is fixed to the liquid-impermeable sheet 3 at a plurality of sections separated from one another in the lateral direction X and the longitudinal direction Y. More specifically, as illustrated in FIG. 3(a) and FIG. 6, the fiber structure member 5 is fixed at a plurality of sections by means of fixing parts 54 and 55 separated from one another in the lateral direction X and the longitudinal direction Y. The fixing parts 55 are arranged along the lateral direction X of the fiber structure member 5, and the fixing parts 54 are arranged along the longitudinal direction Y.

From the viewpoint of fixing the fiber structure member 5 firmly to the liquid-impermeable sheet 3 when applied to the hair, it is preferable that there is at least one section, more preferably at least two sections, fixed in a line along the direction in which the tool is slid on the hair—i.e., the direction of orientation of the hair. More specifically, as illustrated in FIG. 3(a), fixing parts 54 that are long in the longitudinal direction Y are arranged on both sides, in the lateral direction X, of the fiber structure member 5, thereby linearly fixing the fiber structure member 5 to the liquid-impermeable sheet 3. The longitudinal direction Y of the fiber structure member 5 in FIG. 3(a) is the direction in which it is slid on the hair during hair treatment.

Further, from the viewpoint of easy containment and bi-folding of the fiber structure member and from the viewpoint of easy application to the hair, it is preferable that the vicinity of the center of the fiber structure member 5 is fixed discretely in a straight line. More specifically, as illustrated in FIG. 6, before being opened, the packaging 2 and the fiber structure member 5 are folded in two so as to be bisected in the lateral direction X, and a plurality of fixing parts 57 are arranged along the longitudinal direction Y on a folding portion 8 where the fiber structure member is folded in two.

In a planar view, each of the fixing parts 54, 55, 57 for fixing the fiber structure member 5 to the liquid-impermeable sheet 3 may have a discretionary shape, such as circular, elliptic, triangular, square, pentagonal, or heart-shaped. The shapes and sizes of the fixing parts 54, 55, 57 may be the same, or may be different from one another, as illustrated in FIG. 3(a).

The liquid-impermeable sheet 3 preferably forms the packaging 2. More specifically, as illustrated in FIGS. 3(a) and 3(b), the packaging 2 may be formed by joining three sides of the bi-folded liquid-impermeable sheet 3 by means of seal portions 6, 6 and 7. The fiber structure member 5 is contained in the packaging 2 in a state folded in two. With this configuration, when the packaging 2 is opened (torn), the fiber structure member 5 sealed in the packaging 2 is exposed in its spread-out state as illustrated in FIGS. 5(a) to 5(c), and thus, the tool is easier to use and creates no waste.

The same sheet material as described above for the packaging 2 can be used for the liquid-impermeable sheet 3.

The hair treatment tool 1, in which the liquid-impermeable sheet 3 forms the packaging 2, is described in further detail. In the hair treatment tool 1 illustrated in FIG. 3, the packaging 2 is formed of: a sheet 12 forming one surface; and an opposing sheet 13 opposing the sheet 12. More specifically, as illustrated in FIG. 3(b), the packaging 2 has, as outer surfaces, a first surface 2a constituting one surface in the thickness direction and a second surface 2b constituting the other surface in the thickness direction, and the sheet 12 forming the first surface 2a is tearable. In FIG. 3(b), the first surface 2a is the surface—among the two outer surfaces of the packaging 2 formed by the bi-folded double-layered liquid-impermeable sheet 3—in which the notches 91 are provided, and the second surface 2b is the other surface.

Figure 10:
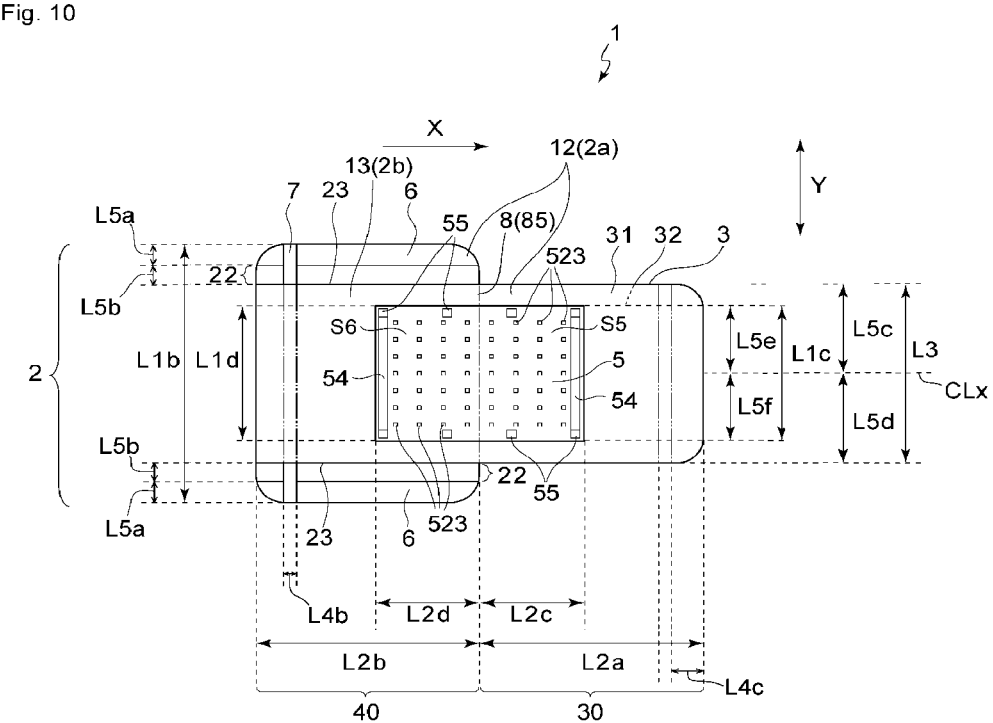
FIG. 10 is a plan view for explaining the dimensions of the hair treatment tool illustrated in FIG. 3(*a*).

In the hair treatment tool 1 illustrated in FIG. 3, the sheet 12, which forms one surface of the packaging 2, is tearable in a manner that creates a gripping piece 30 and a main body portion 40 to which one end of the gripping piece 30 is connected. In the hair treatment tool 1 of the present embodiment, a gripping piece 30 and a main body portion 40 are created, as illustrated in FIG. 10, when the sheet 12, which forms the first surface 2a of the packaging 2, is torn in the tearing direction starting from the tab portion 9 provided at one end of the sheet 12. Stated differently, tearing of the sheet 12 forming the first surface 2a of the packaging 2 creates: a gripping piece 30 constituted by the first surface 2a of the packaging 2; and a main body portion 40 constituted by the second surface 2b of the packaging 2 and portions of the first surface 2a other than the gripping piece 30. In the hair treatment tool 1 illustrated in FIG. 10, the gripping piece 30 and the main body portion 40 are created, with the border being a fold line where the liquid-impermeable sheet 3 is folded in two in the packaging 2; the section where the fold line is located corresponds to a connecting portion 85 where the gripping piece 30 and the main body portion 40 are connected. As described above, by tearing the packaging 2, the hair treatment tool 1 is rendered in a usable state (referred to hereinafter also as "opened state").

In the hair treatment tool 1 of the present embodiment, the gripping piece 30 and the main body portion 40 are formed by a single continuous liquid-impermeable sheet 3, but the main body portion 40 only needs to be connected at one end of the gripping piece 30; for example, the gripping piece 30 and the main body portion 40 do not have to be formed by a single continuous sheet, but the gripping piece 30 and the main body portion 40 may be connected by a joined region provided to one end of the gripping piece 30. In cases where the gripping piece 30 and the main body portion 40 of the hair treatment tool 1 are connected by a joined region, the hair treatment tool 1 is separated into the gripping piece 30 and the main body portion 40, with the joined region serving as the border.

In a planar view of the packaging 2 before opening, the hair treatment tool 1 of the present embodiment includes short sides parallel to one another, and long sides parallel to one another (see FIG. 3(b)). In the packaging 2 before opening, the short sides are parallel to the lateral direction X, and the long sides are parallel to the longitudinal direction Y. In the present embodiment, the lateral direction X is parallel to the tearing direction in which the first surface 2a (liquid-impermeable sheet 3) is torn so as to render the hair treatment tool 1 in an opened state to create the gripping piece 30 and the main body portion 40.

In the hair treatment tool 1 of the present embodiment, the sheet 12 forming the first surface 2a of the packaging 2 is torn from two points separated from one another at one edge of the sheet 12 toward a direction intersecting with the one edge (i.e., along the lateral direction X), to thereby create the gripping piece 30 and the main body portion 40. FIG. 10 illustrates a state in which the gripping piece 30 and the main body portion 40 have been created by tearing the packaging 2's sheet 12 illustrated in FIG. 3(b) from the sheet's one edge provided with the notches 91, 91 up to the position of the liquid-impermeable sheet 3's fold line corresponding to the connecting portion 85. FIG. 10 shows a center line CLx in the longitudinal direction Y that bisects the packaging 2's length in the longitudinal direction Y (which is the same as the main body portion 40's length in the longitudinal direction Y).

As illustrated in FIG. 10, the gripping piece 30 and the main body portion 40 each have an inner surface 31 that had been facing toward inside of the packaging 2. Stated differently, by tearing the packaging 2, the inner surfaces 31 that had been facing toward inside of the packaging 2 are exposed. Note that "the inner surfaces 31 that had been facing toward inside of the packaging 2" refer to the surfaces facing inward in a state before use before tearing and opening the packaging 2.

In an opened state in which the packaging 2 has been torn as illustrated in FIG. 3(a), the fiber structure member 5 is located on the inner surface 31 of each of the gripping piece 30 and the main body portion 40, the respective inner surface being the surface that had been facing toward inside of the packaging 2. More specifically, as illustrated in FIG.

10, a single fiber structure member 5 extending from the gripping piece 30 side to the main body portion 40 side is provided on the inner surfaces that had been facing toward inside of the packaging 2. In the opened state, the fiber structure member 5 may be present so as to span the inner surface 31 of the gripping piece 30 and the inner surface 31 of the main body portion 40. Alternatively, a separate fiber structure member 5 may be present on each of the inner surface 31 of the gripping piece 30 and the inner surface 31 of the main body portion 40, i.e., each inner surface 31 may be provided with respective fiber structure members 5.

In the opened state, the fiber structure member 5 does not have to be fixed on one or both of the inner surfaces 31 of the gripping piece 30 and/or the main body portion 40. More specifically, a fiber structure member 5 retaining a highly viscous hair cosmetic may be positioned on the respective inner surfaces 31 of the gripping piece 30 and the main body portion 40 by sticking to the respective inner surfaces 31 of the gripping piece 30 and the main body portion 40. Alternatively, a fiber structure member 5 made using a highly flexible material may be contained in a folded state inside the packaging 2, and, when the gripping piece 30 and the main body portion 40 are created by tearing the packaging, the fiber structure member 5 may be spread open and be positioned on the respective inner surfaces 31 of the gripping piece 30 and the main body portion 40.

When the packaging 2 is torn open, the fiber structure member 5 contained therein is exposed, as described above. The fiber structure member 5 retains the hair cosmetic, and by bringing the fiber structure member 5 into contact with the hair, or preferably by bringing the hair into contact with the fiber structure member 5 by sandwiching it between the gripping piece 30 and the main body portion 40, the hair cosmetic retained by the fiber structure member 5 is transferred to the hair, and thereby, the hair can be treated by the hair cosmetic. By retaining the hair cosmetic in the fiber structure member 5, it is possible to prevent the hair cosmetic from inadvertently spilling outside the hair treatment tool 1 upon tearing the packaging 2, and also prevent the hair cosmetic from adhering to the handler's fingers, etc. Further, at the time of applying the hair cosmetic to the hair using the hair treatment tool 1, the handler can adjust the amount of application more easily, and treatment can be performed more efficiently within a desired application area.

By tearing the hair treatment tool 1 so as to create the gripping piece 30 and the main body portion 40, the hair treatment tool is rendered in an opened state. As illustrated in FIG. 10, the respective widths, in the longitudinal direction Y, of the gripping piece 30 and the main body portion 40 are different from one another. Stated differently, the dimensions of the gripping piece 30 and the main body portion 40 are asymmetric, which makes the tool easy to hold (easy to pinch with the hand), thereby allowing the task of applying the hair cosmetic to the hair, as described further below, to be performed easily. Further, in the hair treatment tool 1, the fiber structure member 5 is located on the respective inner surfaces of the gripping piece 30 and the main body portion 40, and thus, the hair cosmetic can be applied easily, and also, the tool can be used favorably, particularly in cases of applying the hair cosmetic to the hair while sandwiching the hair between the packaging. Furthermore, since the hair treatment tool 1 is rendered in a usable state (opened state) by being torn so as to create the gripping piece 30 and the main body portion 40, no unnecessary parts (waste), such as peeled sheets, will arise upon use. Thus, the hair treatment tool 1 illustrated in FIG. 3 is easy to use.

Preferably, a portion, or the entirety, of the section of the fiber structure member 5 located on the gripping piece 30 is fixed to the inner surface 31 of the gripping piece 30. When the packaging 2 is torn, the fiber structure member 5 is exposed together with the inner surfaces 31 of the gripping piece 30 and the main body portion 40; fixing a portion of the fiber structure member 5 to the inner surface of the gripping piece 30 facilitates the application task, without causing the fiber structure member 5 to fall off, when applying the hair cosmetic to the hair, such as the hair on one's head, with the hair treatment tool 1 whose packaging 2 has been opened, as described further below. Also, the gripping piece 30 can support the fiber structure member 5 more easily when sandwiching the hair between the gripping piece 30 and the main body portion 40, and handleability upon applying the hair cosmetic to the hair is further improved.

From the same viewpoint, it is preferable that a portion, or the entirety, of the section of the fiber structure member 5 located on the main body portion 40 is fixed to the inner surface 31 of the main body portion 40. Fixing a portion of the fiber structure member 5 to the inner surface of the main body portion 40 facilitates application, without causing the fiber structure member 5 to fall off, when applying the hair cosmetic to the hair, such as the hair on one's head, with the hair treatment tool 1 whose packaging 2 has been opened. Also, the main body portion 40 can support the fiber structure member 5 more easily when sandwiching the hair between the gripping piece 30 and the main body portion 40, and handleability upon applying the hair cosmetic to the hair is further improved.

More preferably, the fiber structure member 5 is fixed to both the inner surface 31 of the gripping piece 30 and the inner surface 31 of the main body portion 40. By fixing it to both inner surfaces 31, the hair can be sandwiched between the fiber structure member 5, and, when performing treatment while moving the fiber structure member 5 in a state sandwiching the hair, the treatment task can be performed more efficiently. Also, the hair cosmetic can be applied more uniformly to the surface of the hair. Furthermore, when treating the hair by using a packaging 2 in which separate fiber structure members 5 are present respectively on the inner surface 31 of the gripping piece 30 and the inner surface 31 of the main body portion 40, the fiber structure members 5 are supported by the gripping piece 30 and the main body portion 40 more easily.

The expression "the fiber structure member 5 is located on the inner surface 31 of the gripping piece 30" (or "located on the inner surface 31 of the main body portion 40") encompasses: cases where the fiber structure member is fixed to the inner surface 31; cases where the fiber structure member is present in a state of contact with the inner surface 31; and cases where the fiber structure member 5 is located vertically above the inner surface of the gripping piece 30 (or the main body portion 40) in a horizontally spread-open state in which the opened hair treatment tool 1 is placed on a horizontal plane, with the side having the fiber structure member 5 facing vertically upward, and the gripping piece 30 and the main body portion 40 are spread in a single plane. It is, however, preferable that the fiber structure member is fixed to the inner surface of the gripping piece 30, or in contact with the inner surface of the gripping piece 30 even in a horizontally spread-open state. Also, preferably, the fiber structure member is fixed to the inner surface of the main body portion 40, or in contact with the inner surface of the main body portion 40 even in a horizontally spread-open state.

In the present embodiment, portions of the fiber structure member 5 are fixed to the inner surface 31 of the gripping piece 30 by means of first fixing parts 55 and a second fixing part 54 (see FIG. 10). As illustrated in FIG. 10, the fiber structure member 5 and the gripping piece 30's inner surface 31, as well as the fiber structure member 5 and the main body portion 40's inner surface 31, are joined together by the first fixing parts 55 and the second fixing parts 54. The first fixing parts 55 are formed on both end sides, in the longitudinal direction Y, of the fiber structure member 5 at four locations separated from one another in the lateral direction X. The second fixing parts 54 are formed so as to extend along the longitudinal direction Y at respective end sides, in the lateral direction X, of the fiber structure member 5.

Instead of partially joining the fiber structure member 5 and the gripping piece 30's inner surface 31 at one or more sections, they may be joined together over the entire region of the gripping piece 30. Also, instead of partially joining the fiber structure member 5 and the main body portion 40's inner surface 31 at one or more sections, they may be joined together over the entire region of the main body portion 40.

From the viewpoint of facilitating hair treatment, as illustrated in FIG. 3, it is preferable that, in the hair treatment tool 1, the fiber structure member 5 is arranged on the inner-side surface of the bi-folded liquid-impermeable sheet 3, so that the fiber structure member 5 faces itself. More specifically, it is preferable that the fiber structure member 5 is arranged in a state in which the fiber structure member 5 spans a folding portion 8 at which the liquid-impermeable sheet 3 is folded in two, in a manner that the surfaces of the fiber structure member 5 that come into contact with the hair face one another when sandwiching the hair with the hair treatment tool.

This configuration is described in detail. Preferably, a portion of the fiber structure member 5 located on the main body portion 40 and a portion thereof located on the gripping piece 30 are continuous; and the fiber structure member 5 is contained in the packaging 2 in a folded state in a manner that a folding portion 8 located between the two portions is located on the connecting portion side where the gripping piece 30 and the main body portion 40 are connected. More specifically, as illustrated in FIG. 10, the fiber structure member 5 is a single sheet in which, in an opened state, the portion of the fiber structure member 5 located on the main body portion 40 and the portion thereof located on the gripping piece 30 are continuous. Further, as illustrated in FIG. 10, the fiber structure member 5 has a folding portion 8 between the portion located on the main body portion 40 and the portion located on the gripping piece 30. Before the packaging 2 is opened, the fiber structure member 5 is contained in the packaging 2 in a state where the fiber structure member 5 is folded, in a manner that the folding portion 8 is located on the connecting portion 85 (fold line) side where the gripping piece 30 and the main body portion 40 are connected (this configuration is not illustrated). The fiber structure member 5 in a state before the packaging 2 is opened may be folded in two, with the connecting portion 85 between the main body portion 40 and the gripping piece 30 serving as a border, or may be folded a plurality of times in three or more. Preferably, the fiber structure member 5, which is contained in a folded state, is arranged so that, in an opened state, it spreads out on the respective inner surfaces of the gripping piece 30 and the main body portion 40.

From the viewpoint of further facilitating the task of applying the hair cosmetic to the hair, the area of the fiber structure member 5 is preferably 4 $cm^2$ or greater, more preferably 6 $cm^2$ or greater, and preferably 250 $cm^2$ or less, more preferably 200 $cm^2$ or less, and preferably from 4 to 250 $cm^2$, more preferably from 6 to 200 $cm^2$.

Preferably, the portion of the fiber structure member 5 located on the main body portion 40 and the portion thereof located on the gripping piece 30 have the same area. By making the area S5 of the portion of the fiber structure member 5 located on the gripping piece 30 the same as the area S6 of the portion located on the main body portion 40, a more sufficient amount of hair cosmetic can be applied to the hair more uniformly. The area S5 of the portion of the fiber structure member 5 located on the gripping piece 30, as well as the area S6 of the portion located on the main body portion 40, is preferably 2 $cm^2$ or greater, more preferably 3 $cm^2$ or greater, and preferably 125 $cm^2$ or less, more preferably 100 $cm^2$ or less, and preferably from 2 to 125 $cm^2$, more preferably from 3 to 100 $cm^2$. Herein, "same" in the expression "the portion located on the main body portion 40 and the portion located on the gripping piece 30 have the same area" means that the area S5 of the portion located on the gripping piece 30 is from 80 to 120%, more preferably from 90 to 110%, the area S6 of the portion located on the main body portion 40.

The fiber structure member 5 retains the hair cosmetic, and for the retention method, any discretionary method can be employed for retaining the hair cosmetic with the fiber structure member 5, depending on the properties of the hair cosmetic. For example, in cases where the hair cosmetic is a liquid, the fiber structure member 5 can retain the hair cosmetic by impregnating the fiber structure member 5 with the hair cosmetic.

As will be described below, the hair treatment tool 1 illustrated in FIG. 3 can apply the hair cosmetic to the hair by sandwiching the hair on one's head (referred to hereinafter also as "hair") between the gripping piece 30 and the main body portion 40. More specifically in the present embodiment, treatment with the hair treatment tool 1 can be performed by: sandwiching the hair between the gripping piece 30 and the main body portion 40, to bring the fiber structure member 5, which is supported by the gripping piece 30 and the main body portion 40, into contact with the hair; and transferring the hair cosmetic retained by the fiber structure member 5 onto the hair. As described above, since the hair can be treated by the hair cosmetic simply by being sandwiched between the gripping piece 30 and the main body portion 40—more specifically, between the fiber structure member 5—the operation of performing treatment with the hair treatment tool 1 illustrated in FIG. 3 is extremely easy. Further, by sliding the hair treatment tool 1 in the longitudinal direction Y with the hair sandwiched therebetween, the hair cosmetic can be applied uniformly to the surface of the hair. Furthermore, when performing treatment with the hair treatment tool 1, the hair cosmetic can be prevented from contacting the handler's skin, such as the fingers.

From the viewpoint of further facilitating the handler's perception of the contact between the fiber structure member 5 and the hair, the length (L2d+L2c) of the fiber structure member 5 along the lateral direction X with respect to the length (L2b+L2a) of the liquid-impermeable sheet 3 along the lateral direction X is preferably 25% or greater, more preferably 30% or greater, and preferably 97% or less, more preferably 80% or less, and preferably from 25 to 97%, more preferably from 30 to 80%.

From the viewpoint of allowing the hair cosmetic to be applied more uniformly to the hair, the length (L2a) of the gripping piece 30 along the lateral direction X with respect to the length (L2b) of the main body portion 40 along the lateral direction X is preferably 50% or greater, more preferably 60% or greater, even more preferably 75% or greater, and preferably 200% or less, more preferably 180% or less, even more preferably 150% or less, and preferably from 50 to 200%, more preferably from 60 to 180%, even more preferably from 75 to 150%.

From the viewpoint of further facilitating the task of transferring the hair cosmetic to the hair, the length (L2c), along the lateral direction X, of the fiber structure member 5 on the gripping piece 30 with respect to the length (L2d), along the lateral direction X, of the fiber structure member 5 on the main body portion 40 is preferably 75% or greater, more preferably 80% or greater, and preferably 130% or less, more preferably 120% or less, and preferably from 75 to 130%, more preferably from 80 to 120%. From the viewpoint of allowing the hair cosmetic to be applied more uniformly, it is more preferable that the length (L2d), along the lateral direction X, of the fiber structure member 5 on the main body portion 40 and the length (L2c) of the fiber structure member 5 on the gripping piece 30 are similar, even more preferably the same.

From the viewpoint of further facilitating the handler's perception of the contact between the fiber structure member 5 and the hair, the length (L2d), along the lateral direction X, of the fiber structure member 5 on the main body portion 40 with respect to the length (L2b) of the main body portion 40 along the lateral direction X is preferably 25% or greater, more preferably 30% or greater, and preferably 97% or less, more preferably 80% or less, and preferably from 25 to 97%, more preferably from 30 to 80%.

From the viewpoint of further facilitating the handler's perception of the contact between the fiber structure member 5 and the hair, the length (L2c), along the lateral direction X, of the fiber structure member 5 on the gripping piece 30 with respect to the length (L2a) of the gripping piece 30 along the lateral direction X is preferably 25% or greater, more preferably 30% or greater, and preferably 97% or less, more preferably 80% or less, and preferably from 25 to 99%, more preferably from 30 to 80%.

From the viewpoint of easy openability using the tab portion and easy tearing of the gripping piece 30, the length (L4c) of the tab portion 9 along the lateral direction X with respect to the length (L2a) of the gripping piece 30 along the lateral direction X is preferably 1% or greater, more preferably 2% or greater, even more preferably 5% or greater, and preferably 30% or less, more preferably 25% or less, even more preferably 20% or less, and preferably from 1 to 30%, more preferably from 2 to 25%, even more preferably from 5 to 20%. The length L4c of the tab portion 9 along the lateral direction X is the length from the gripping piece 30's end, in the lateral direction X, on the tear-starting side to the opening seal portion 7's end on the tear-starting side (see FIG. 10).

From the viewpoint of hermeticity of the packaging 2 and easy openability upon opening, the length (L4b) of the opening seal portion 7 along the lateral direction X with respect to the length (L2b or L2a) of the main body portion 40 or the gripping piece 30 along the lateral direction X is preferably 1% or greater, more preferably 2% or greater, even more preferably 5% or greater, and preferably 30% or less, more preferably 25% or less, even more preferably 20% or less, and preferably from 1 to 30%, more preferably from 2 to 25%, even more preferably from 5 to 20%.

From the viewpoint of further facilitating the handler's perception of the contact between the fiber structure member 5 and the hair, the length (L1d) of the fiber structure member 5 along the longitudinal direction Y with respect to the length (L1b) of the liquid-impermeable sheet 3 along the longitudinal direction Y is preferably 30% or greater, more preferably 35% or greater, even more preferably 40% or greater, and preferably 95% or less, more preferably 90% or less, even more preferably 80% or less, and preferably from 30 to 95%, more preferably from 35 to 90%, even more preferably from 40 to 80%. The length of the liquid-impermeable sheet 3 along the longitudinal direction Y is the same as the length of the main body portion 40 along the longitudinal direction Y.

From the viewpoint of further facilitating the handler's perception of the contact between the fiber structure member 5 and the hair, the length (L3) of the gripping piece 30 along the longitudinal direction Y with respect to the length (L1b) of the main body portion 40 along the longitudinal direction Y is preferably 35% or greater, more preferably 40% or greater, even more preferably 50% or greater, and preferably 98% or less, more preferably 90% or less, even more preferably 80% or less, and preferably from 35 to 98%, more preferably from 40 to 90%, even more preferably from 50 to 80%. The length of the main body portion 40 along the longitudinal direction Y is the same as the length of the liquid-impermeable sheet 3 along the longitudinal direction Y.

From the viewpoint of further preventing the adhesion of the hair cosmetic to the skin etc. of the handler handling the hair treatment tool 1, the length (L1d) of the fiber structure member 5 along the longitudinal direction Y with respect to the length (L3) of the gripping piece 30 along the longitudinal direction Y is preferably 50% or greater, more preferably 55% or greater, even more preferably 60% or greater, and preferably 99% or less, more preferably 90% or less, even more preferably 85% or less, and preferably from 50 to 99%, more preferably from 55 to 90%, even more preferably from 60 to 85%.

From the viewpoint of hermeticity of the packaging 2 and easy openability upon opening, the length (L5a) of the fixing seal portion 6 along the longitudinal direction Y with respect to the length (L1b) of the liquid-impermeable sheet 3 along the longitudinal direction Y is preferably 1% or greater, more preferably 2% or greater, and preferably 15% or less, more preferably 10% or less, and preferably from 1 to 15%, more preferably from 2 to 10%. The length of the liquid-impermeable sheet 3 along the longitudinal direction Y is the same as the length of the main body portion 40 along the longitudinal direction Y.

From the viewpoint of further facilitating the handler's perception of the contact between the fiber structure member 5 and the hair, it is preferable to arrange the fiber structure member 5 so as to evenly lie across the liquid-impermeable sheet 3's center line CLx in the longitudinal direction Y, but the fiber structure member may be arranged in an unbalanced manner along the longitudinal direction Y. The fiber structure member 5's length (L5e), along the longitudinal direction Y, on one side from the liquid-impermeable sheet 3's center line CLx in the longitudinal direction Y with respect to the length (L5f) on the other side is preferably 70% or greater, more preferably 75% or greater, even more preferably 80% or greater, and preferably 140% or less, more preferably 130% or less, even more preferably 120% or less, and preferably from 70 to 140%, more preferably from 75 to 130%, even more preferably from 80 to 120%. Herein, the fiber structure member 5's length (L5e), along the longitudinal direction Y, on one side from the liquid-impermeable sheet 3's center line CLx in the longitudinal direction Y is, as illustrated in FIG. 10, the length, in the longitudinal direction Y, of the fiber structure member 5 on the upper side of the center line CLx when the hair treatment tool 1 is placed so that the gripping piece 30 is on the right and the main body portion 40 is on the left in an opened state, and the fiber structure member 5's length (L5f), along the longitudinal direction Y, on the other side is the length, in the longitudinal direction Y, of the fiber structure member 5 on the lower side of the center line CLx.

From the viewpoint of further facilitating the handler's perception of the contact between the fiber structure member 5 and the hair, with respect to the gripping piece 30's length (L5c), along the longitudinal direction Y, on one side from the liquid-impermeable sheet 3's center line CLx in the longitudinal direction Y, the fiber structure member 5's length (L5e) along the longitudinal direction Y located on the same side as the gripping piece 30 with respect to the center line CLx is preferably 25% or greater, more preferably 30% or greater, even more preferably 40% or greater, and preferably 99% or less, more preferably 90% or less, even more preferably 85%, and preferably from 25 to 99%, more preferably from 30 to 90%, even more preferably from 40 to 85%.

From the same viewpoint, with respect to the gripping piece 30's length (L5d), along the longitudinal direction Y, on the other side from the liquid-impermeable sheet 3's center line CLx in the longitudinal direction Y, the fiber structure member 5's length (L5f) along the longitudinal direction Y located on the same side as the gripping piece 30 with respect to the center line CLx is preferably 25% or greater, more preferably 30% or greater, even more preferably 40% or greater, and preferably 99% or less, more preferably 90% or less, even more preferably 85%, and preferably from 25 to 99%, more preferably from 30 to 90%, even more preferably from 40 to 85%.

From the viewpoint of further facilitating the task of transferring the hair cosmetic to the hair, the length (L1b) of the liquid-impermeable sheet 3 along the longitudinal direction Y with respect to the length (L2b+L2a) of the liquid-impermeable sheet 3 along the lateral direction X is preferably 10% or greater, more preferably 20% or greater, even more preferably 25% or greater, and preferably 1000% or less, more preferably 500% or less, even more preferably 400%, and preferably from 10 to 1000%, more preferably from 20 to 500%, even more preferably from 25 to 400%.

From the viewpoint of further facilitating the task of transferring the hair cosmetic to the hair, the length (L1d) of the fiber structure member 5 along the longitudinal direction Y with respect to the length (L2d+L2c) of the fiber structure member 5 along the lateral direction X is preferably 10% or greater, more preferably 20% or greater, even more preferably 25% or greater, and preferably 1000% or less, more preferably 500% or less, even more preferably 400%, and preferably from 10 to 1000%, more preferably from 20 to 500%, even more preferably from 25 to 400%.

The preferable dimensions of the various parts as described above, as well as the ratios based on those dimensions, are values measured in an opened state as illustrated in FIG. 10, and preferably in the aforementioned horizontally spread-open state, or are calculated based on those values.

As described above, the liquid-impermeable sheet 3 of the hair treatment tool 1 preferably has tear rectilinearity in the tearing direction (lateral direction X). Providing tear rectilinearity in the tearing direction can further facilitate tearing (opening) of the hair treatment tool 1 and can also prevent the fiber structure member 5 from getting torn together with the liquid-impermeable sheet 3 upon opening. "Tear rectilinearity" refers to a property or structure that is easily torn rectilinearly in a specific direction. Examples of sheets having tear rectilinearity include: a sheet having a cut line, such as a half-cut line, that does not penetrate the sheet in the thickness direction and that is provided rectilinearly along a specific direction; and a film material in which a polymer is oriented so that it tears easily in a specific direction by stretching.

More specifically, as illustrated in FIG. 3(b), the liquid-impermeable sheet 3 has, at an opening start portion for starting the tearing of the liquid-impermeable sheet 3, notches 91, 91 that are cut along the tearing direction at both ends of the tab portion 9. In order to clearly indicate the position of the opening start portion to allow the handler to perform tearing smoothly, a line along the tearing direction starting from the opening start portion may be printed on the packaging 2. Further, depending on the position of the gripping piece 30, a plurality of the aforementioned cut lines may be provided to the liquid-impermeable sheet 3 in a rectilinear, zigzag, or curved shape. From the viewpoint of making it more easy to start tearing at the opening start portion, it is preferable that the packaging 2 has, at the opening start portion, a notch, a cut, a printed mark, or a combination of the above. In the packaging 2 of the present embodiment, the opening start portion is the tab portion 9 on the first surface 2a (see FIG. 3(b)). The packaging 2's end portion on the opening start portion side is the tear starting end of the liquid-impermeable sheet 3, whereas the packaging 2's end portion on the opposite side from the tear starting end is the tear termination end of the liquid-impermeable sheet 3.

Preferably, the main body portion 40 has a pocket portion 22 on one side, or pocket portions 22 on both sides, in the direction (longitudinal direction Y) intersecting with the tearing direction of the liquid-impermeable sheet 3. In the present embodiment, as illustrated in FIG. 10, tearing the first surface 2a of the packaging 2 forms opening edges 23, 23 separated from one another in the longitudinal direction Y. In the present embodiment, the packaging 2 of the hair treatment tool 1 in an opened state has pocket portions 22, 22 formed along the tearing direction and formed between the respective opening edges 23 and the respective fixing seal portions 6 located on both sides in the longitudinal direction Y. The pocket portions 22 each have a space in the interior thereof. Thus, any hair cosmetic that was not held on the hair can be received in the pocket portions 22. Particularly in cases where the hair cosmetic is a liquid, when liquid leakage occurs from the fiber structure member 5 upon pressing the gripping piece 30 and the main body portion 40 with great force, the pocket portions 22 can catch this liquid leakage, and thereby, the hair cosmetic can be inhibited from dripping outside the hair treatment tool 1.

From the viewpoint of achieving the aforementioned effects more reliably, the depth (L5b) of each pocket portion 22 with respect to the main body portion 40's maximum length L1b along the longitudinal direction Y is preferably 1% or greater, more preferably 2% or greater, and preferably 20% or less, more preferably 18% or less, and preferably from 1 to 20%, more preferably from 2 to 18%. The depth (L5b) of each pocket portion 22 refers to the length, in the longitudinal direction Y, from the opening edge 23 to the fixing seal portion 6 (see FIG. 10).

In cases where the pocket portions 22 are formed respectively on both sides in the longitudinal direction Y, the pocket portions 22 may both have the same depth, or may have different depths. For example, the depth of the pocket portion 22 on the lower side when the hair treatment tool 1 is sandwiching the hair may be greater than the depth of the pocket portion 22 on the upper side.

Figure 11:
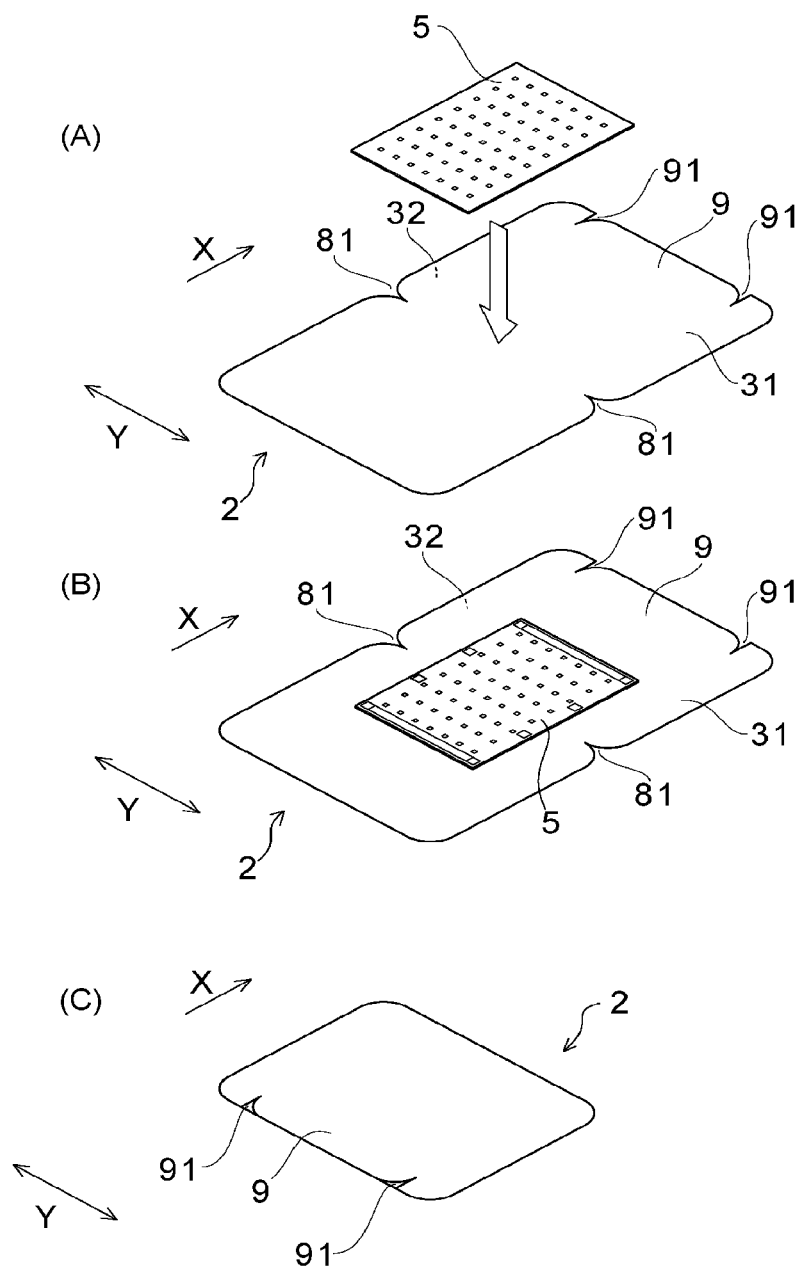
Figure 12:
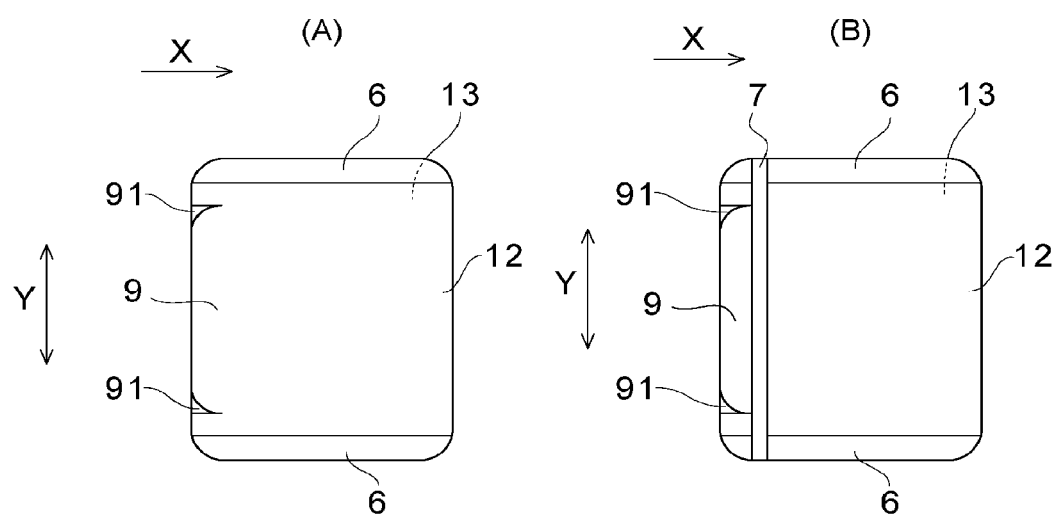

FIGS. 11 and 12 illustrate a method for manufacturing a hair treatment tool 1 according to the present embodiment. In this method for manufacturing a hair treatment tool 1, a fiber structure member 5 is placed on the inner surface 31 of a liquid-impermeable sheet 3 (FIG. 11(A)), and then, the fiber structure member 5 is fixed to the inner surface 31 on the gripping piece 30 side, or on the inner surface 31 of the gripping piece 30 and the main body portion 40 (FIG. 11(A)). Then, the liquid-impermeable sheet 3 is folded up in two so that the fiber structure member 5 is arranged inside the liquid-impermeable sheet 3 (FIG. 11(C)). Next, to the folded liquid-impermeable sheet 3, fixing seal portions 6 parallel to the tearing direction are formed on both sides in the direction Y intersecting with the tearing direction (lateral direction X) (FIG. 12(A)). Then, to the liquid-impermeable sheet 3 provided with the fixing seal portions 6, an opening seal portion 7 is formed on the starting end side of the tearing direction (FIG. 12(B)), to obtain the hair treatment tool 1. The hair cosmetic is retained by the retaining element before forming the opening seal portion 7.

As for methods for fixing the fiber structure member 5 to the liquid-impermeable sheet 3 and methods for forming the fixing seal portions 6 and the opening seal portion 7 in the liquid-impermeable sheet 3, it is possible to employ various known means, such as adhesive application methods, and fusion-bonding/fixing methods such as heat sealing, ultrasonic sealing, high-frequency sealing, or the like.

It is preferable to make the fiber structure member 5 retain the hair cosmetic after the fiber structure member is fixed to the inner surface 31 of the liquid-impermeable sheet 3. The hair cosmetic usable herein may be in the form of a liquid, viscous material (cream), or powder. An example of a method for making the fiber structure member 5 retain the hair cosmetic is to first fix the fiber structure member 5, such as a nonwoven fabric, onto the inner surface 31 of the liquid-impermeable sheet 3, and then impregnate the fiber structure member 5 with the hair cosmetic such as by spraying. The hair cosmetic may be retained by the fiber structure member 5 before forming the fixing seal portions 6 (the state of FIG. 3(b)), or after forming the fixing seal portions 6 and before forming the opening seal portion 7 (the state of FIG. 12(A)).

In addition to the notches 91, 91 provided at both ends, in the Y direction, of the tab portion 9 for imparting the aforementioned tear rectilinearity, the liquid-impermeable sheet 3 of the present embodiment also includes notches 81, 81, as fold guide portions, in a central section in the tearing direction (lateral direction X) on both end sides of the liquid-impermeable sheet 3. The notches 81 are located respectively at both end sides, in the longitudinal direction Y, of the connecting portion 85, which is the fold section upon folding up the liquid-impermeable sheet 3. FIG. 11(C) illustrates a state in which the liquid-impermeable sheet 3 is folded in two between the notches 81. Note that the notches 81 may be provided as in the present embodiment, but do not need to be provided.

The planar-view shape of the hair treatment tool 1 illustrated in FIG. 3 is not limited to rectangular, and may be any discretionary shape, such as circular, elliptic, or square. Further, the hair treatment tool 1 illustrated in FIG. 3 is a rectangle in which the long sides are in the longitudinal direction in a planar view, but it may be a rectangle in which the long sides are in the lateral direction. Further, the packaging 2 of the present embodiment is rectangular with its corners rounded, but the corners do not have to be rounded.

Preferably, the packaging 2 has at least one fixing seal portion where the liquid-impermeable sheet 3 is joined with an opposing sheet opposing the liquid-impermeable sheet 3, the fixing seal portion being provided on one side, or the fixing seal portions being provided on both sides, in the direction Y intersecting with the tearing direction (lateral direction X) of the liquid-impermeable sheet 3. More specifically, as illustrated in FIG. 12, the liquid-impermeable sheet 3 folded in two in FIG. 11(C) has fixing seal portions 6 formed so as to join the sheet forming the first surface 2a of the packaging and the sheet opposing the aforementioned sheet and forming the second surface 2b. As illustrated in FIG. 12(A), on the respective inner surfaces of the sheet forming the packaging 2's first surface 2a and the sheet forming the second surface 2b, the fixing seal portions 6, which are parallel to the tearing direction, are formed on both sides in the direction Y intersecting with the tearing direction of the liquid-impermeable sheet 3. The fixing seal portions 6 of the packaging 2 formed as above join the bi-folded double-layered liquid-impermeable sheet 3 at both sides in the longitudinal direction Y.

Preferably, the packaging 2 has an opening seal portion 7 where the liquid-impermeable sheet 3 is joined with an opposing sheet opposing the sheet, the opening seal portion 7 being provided more toward the starting end side than the central position in the tearing direction (lateral direction X) of the liquid-impermeable sheet 3. More specifically, to the liquid-impermeable sheet 3 provided with the fixing seal portions as illustrated in FIG. 12(A), an opening seal portion 7 is formed on the starting end side in the tearing direction (see FIG. 12(B)). By joining the liquid-impermeable sheet 3 and the opposing sheet with the fixing seal portions 6, 6 and the opening seal portion 7, the fiber structure member 5 can be contained in a hermetically sealed state, and thereby, the storability of the hair cosmetic can be further improved. Further, because the fiber structure member 5 is contained in a hermetically sealed state, the hair cosmetic can be prevented from leaking and causing soiling, and also, portability is further improved, thus enhancing usability in various situations, such as outside the home.

Also from the viewpoint of further facilitating the task of tearing the packaging 2, it is preferable that the sealing strength of the fixing seal portions 6 is stronger than that of the opening seal portion 7.

Figure 5:
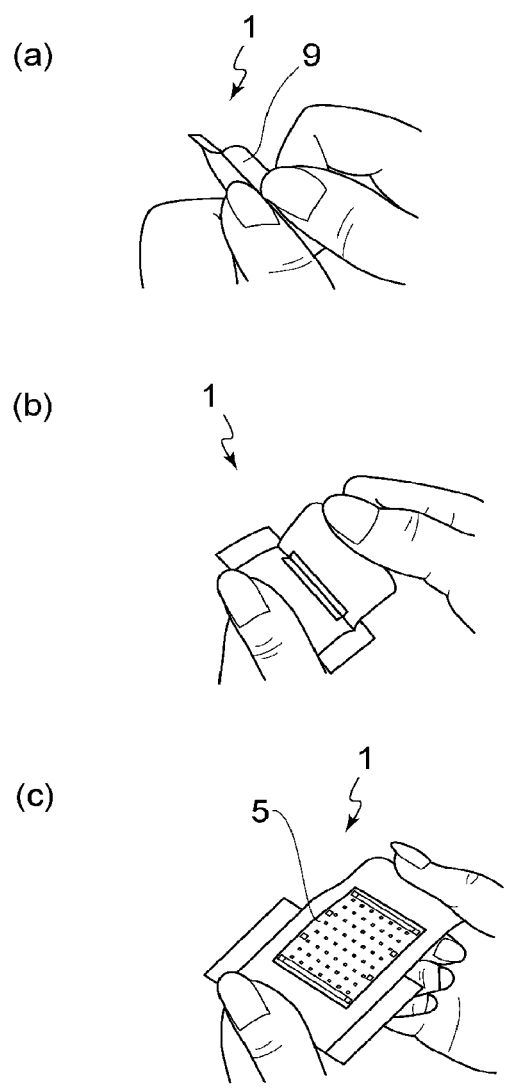
FIG. 5 illustrates schematic diagrams illustrating how the hair treatment tool illustrated in FIG. 3 is opened.

Preferably, the opening seal portion 7 is located more toward the termination end side in the tearing direction than the tear starting end portion, i.e., the end portion on the starting end side in the tearing direction (lateral direction X). As illustrated in FIG. 12, preferably, the opening seal portion 7 is located at a distance from the end portion side where tearing of the packaging 2 is started. This is because a tab portion 9 is provided to allow biparting of the liquid-impermeable sheet 3 along the longitudinal direction Y, as illustrated in FIG. 5, which is described further below. Stated differently, as illustrated in FIG. 5, in the packaging 2, the double layers of the liquid-impermeable sheet 3 are not joined together at the tab portion 9 for starting tearing, and thus, biparting of the sheets 3 is possible along the longitudinal direction Y. This further facilitates the tearing task.

Preferably, in the direction Y intersecting with the tearing direction (lateral direction X), the tearing position of the liquid-impermeable sheet 3 is located more toward the central side than the seal portions (the fixing seal portions 6, 6 in the present embodiment) where the sheet 12 and the opposing sheet 13 opposing the sheet 12 are joined. This is to further facilitate the task of tearing the packaging 2 and to further prevent the fiber structure member 5 from getting torn together with the first surface 2a of the packaging 2. The tearing position of the liquid-impermeable sheet 3 in the present embodiment is the region between the notches 91 and the region between the opening edges 23 in the longitudinal direction Y of FIG. 10.

In the hair treatment tool 1, preferably, the sheets at the seal portion (the opening seal portion 7 in the present embodiment) joining the liquid-impermeable sheets 3 along the direction Y intersecting with the tearing direction are peeled apart when the packaging 2 (the liquid-impermeable sheet 3) is torn so as to create the gripping piece 30 and the main body portion 40. This is to further facilitate the tearing task. On the other hand, from the same viewpoint, it is preferable that the fixing seal portions 6, 6 join the first surface 2a and the second surface 2b of the liquid-impermeable sheet 3 in an unpeelable manner. Stated differently, preferably, the fixing seal portions 6, 6 joining the liquid-impermeable sheets 3 along the tearing direction join the liquid-impermeable sheets 3 in an unpeelable manner.

In FIG. 12, the opening seal portion 7 is formed after the fixing seal portions 6, 6, but the opening seal portion 7 may be formed first. For the formation of the fixing seal portions 6 and the opening seal portion 7, one of various known joining means may be used, such as ultrasonic sealing, heat sealing, high-frequency sealing, or an adhesive.

FIG. 5 illustrates steps for tearing and opening the hair treatment tool 1. In the hair treatment tool 1 illustrated in FIG. 3, the liquid-impermeable sheet 3 is bipartable (can be opened away from each other) at the tab portion 9 as illustrated in FIG. 5(A). Preferably, notches 91, 91 are formed on both end portions, in the longitudinal direction Y, of the tab portion 9. This is to impart rectilinearity in the tearing direction.

Next, tearing of the liquid-impermeable sheet 3 forming the first surface 2a of the packaging 2 is started from the tab portion 9, and the sheet is torn in the tearing direction (lateral direction X) (FIG. 5(B)). This tearing causes the opening seal portion 7 to be peeled apart.

Completely tearing the liquid-impermeable sheet 3 constituting the first surface 2a causes the fiber structure member 5 and the inner surface 31, on the fiber structure member 5's side that comes into contact with the hair, to be exposed (FIG. 5(C)).

Preferably, the hair to be treated with the hair treatment tool of the invention is, for example, the hair on one's head. The hair cosmetic of the hair treatment tool according to the invention includes a pigment.

Conventional hair dyeing tools have difficulty in uniformly applying a pigment to the hair and achieving uniform and favorable color development. In contrast, with the hair treatment tool of the present invention, the hair can be colored uniformly and with favorable color development, even in cases where the hair cosmetic includes a pigment.

Any kind of pigment can be employed as the pigment included in the hair cosmetic, regardless of, for example, the form (spherical, acicular, tabular, etc.), particle size, or particle structure (porous, imperforated, etc.). Examples include inorganic pigments, organic pigments, pearl pigments, metal powder pigments, and glittering powders.

Concrete examples of inorganic pigments include: inorganic black pigments such as carbon black, iron oxide black, and titanium oxide black; inorganic red pigments such as iron oxide (colcothar), iron hydroxide, and iron titanate; inorganic brown pigments such as γ-iron oxide; inorganic yellow pigments such as iron oxide yellow and loess; inorganic blue pigments such as ultramarine blue and iron blue; inorganic violet pigments such as manganese violet and cobalt violet; inorganic green pigments such as chromium oxide, chromium hydroxide, and cobalt titanate; and inorganic white pigments such as titanium oxide, zinc oxide, and cerium oxide. Preferable among the above are carbon black, iron oxide black, titanium oxide black, iron oxide (colcothar), iron oxide yellow, ultramarine blue, and iron blue.

Examples of organic pigments include Red No. 201, Red No. 202, Red No. 203, Red No. 204, Red No. 205, Red No. 206, Red No. 207, Red No. 208, Red No. 219, Red No. 220, Red No. 221, Red No. 228, Red No. 404, Red No. 405, Orange No. 203, Orange No. 204, Orange No. 401, Yellow No. 205, Yellow No. 401, and Blue No. 404. Preferable among the above are Red No. 202, Red No. 404, Yellow No. 205, Yellow No. 401, and Blue No. 404.

Examples of pearl pigments include pearl powder, bismuth oxychloride, mica, metal oxide-coated mica (e.g., titanated mica, iron oxide-coated mica, iron oxide-coated titanated mica, iron oxide black-coated mica, iron oxide black-coated titanated mica, iron oxide yellow-coated mica, iron oxide/iron oxide black-coated titanated mica, iron blue-coated titanated mica, iron oxide/iron blue-coated titanated mica, carmine-coated titanated mica, and barium sulfate-coated titanated mica), metal oxide-coated alumina flakes, metal oxide-coated silica flakes, and multilayer-coated pearl pigments (e.g., $TiO_2$-$SiO_2$-$TiO_2$-mica).

Examples of metal powder pigments include gold powder, silver powder, copper powder, aluminum powder, and brass powder.

Examples of glittering powders include polyethylene terephthalate/aluminum/epoxy laminates and polyethylene terephthalate/polyolefin laminated films.

The hair cosmetic includes a solvent. The solvent is not particularly limited, and examples include water and organic solvents permitted to be included in hair cosmetics.

From the viewpoint of preventing problems, such as color staining, caused by adhesion to the hands, clothes, and sections where hair treatment is not desired, it is preferable that the content by percentage of water in the hair cosmetic is 10 mass % or less, more preferably 5 mass % or less. The lower limit of a further preferable range of the content by percentage of water is zero (0) mass %. Water may be deionized water, distilled water, ultrapure water, or tap water.

The aforementioned effects are achieved even more significantly in cases of employing a non-aqueous hair cosmetic which is easy to dry after application. Preferably, the hair cosmetic includes 70 mass % or greater, more preferably 75 mass % or greater, more preferably 80 mass % or greater, of an organic solvent having a boiling point of from 50° C. to 260° C. Further, preferably, the content by percentage of water is 10 mass % or less.

Examples of organic solvents having a boiling point of from 50° C. to 260° C. preferably include ethanol, propanol, propanol, isopropanol, tert-butyl alcohol, 1,3-butylene alcohol, dipropylene glycol, isododecane, and hydrogenated polyisobutene; ethanol and isopropanol are preferred; and ethanol is further preferred. The boiling point of the organic solvent is measured at atmospheric pressure (101.3 kPa).

The hair cosmetic includes a pigment and a film-forming resin, from the viewpoint of: performing coloring with excellent color development regardless of the original hair color, whether black or blond; providing excellent water resistance; and maintaining color without causing secondary adhesion to the face, clothes, etc. Including the film-forming resin allows the hair colored by the hair cosmetic according to the invention to be formed into a desired shape. Further, the color of the hair colored by the hair cosmetic including the pigment and the film-forming resin according to the invention can be removed easily by washing with a shampoo etc.

The film-forming resin is capable of forming a film on the surface of the hair by being applied to the surface of the hair. The scratch hardness (pencil method) of the formed film is preferably softer than 3H, more preferably softer than 2H, more preferably softer than H. More specifically, the scratch hardness (pencil method) is preferably from 6B to 3H, more preferably from 6B to H, more preferably from 6B to H. By employing a resin capable of forming a film whose scratch hardness (pencil method) is within the aforementioned range, the hair can be styled easily into a desired hairstyle. A film for measuring the scratch hardness (pencil method) is prepared by applying 2 g of a 10 mass % ethanol solution of the film-forming resin onto a PET film within a 3-by-4 cm area, and drying the same for 24 hours or longer at 25° C. and relative humidity of 50%.

Examples of the film-forming resin include cationic resins, anionic resins, nonionic resins, and amphoteric resins described below.

Examples of cationic resins that may be used in the invention include vinylpyrrolidone/dimethylaminoethyl methacrylate copolymer diethyl sulfate (H.C. Polymer IS (M), H.C. Polymer 2, etc. (Osaka Organic Chemical Industry Ltd.)), vinylpyrrolidone/dimethylaminopropylmethacrylamide/lauryl dimethylaminopropylmethacrylamide terpolymer (Styleze W-20 (ISP Corp.)), poly(dimethyl methylene piperidinium chloride) (Merquat 100 (Nalco Company)), dimethyldiallylammonium chloride/acrylamide copolymer (Merquat 550 (Nalco Company)), vinylpyrrolidone/N,N-dimethylaminoethyl methacrylate copolymer diethyl sulfate (Gafquat 734 (ISP Corp.)), vinylpyrrolidone/dimethylaminoethyl methacrylate copolymer (Gafquat 440 (ISP Corp.)), N,N-dimethylaminoethyl methacrylate diethyl sulfate/N,N-dimethylacrylamide/polyethylene glycol dimethacrylate terpolymer (Sofcare KG-101W-E, Sofcare KG-301P, etc. (Kao Corporation)), ammonium-modified hydroxyethyl cellulose (SoftCAT SL-30 polymer (Kao Corporation)), N-propionylpolyethyleneimine/methylpolysiloxane copolymer (Elastomer OS (Kao Corporation)), vinylamine/vinylalcohol copolymer (Diafix C-601 (Mitsubishi Chemical Corporation)), polyquaternium-28 (Gafquat HS-100 (Ashland)), polyquaternium-55 (Styleze W-20 (Ashland)), and vinylpyrrolidone/DMAPA acrylate copolymer (Styleze CC-10 (Ashland)). Among the above, from the viewpoint of further reducing stickiness to the hands and fingers upon use and further improving the moist feel, softness, and smoothness of the hair after use, it is preferable to use at least one type of resin selected from the group consisting of dimethyldiallyl ammonium chloride/acrylamide copolymer, vinylpyrrolidone/N,N-dimethylaminoethyl methacrylate copolymer diethyl sulfate, N,N-dimethylaminoethyl methacrylate diethyl sulfate/N,N-dimethylacrylamide/polyethylene glycol dimethacrylate terpolymer, and ammonium-modified hydroxyethyl cellulose, and more preferable to use N-propionylpolyethyleneimine/methylpolysiloxane copolymer.

Examples of anionic resins include methacrylic acid/1,1-dimethylethyl acrylate/ethyl acrylate terpolymer (Luvimer 100P, Luvimer 30E (BASF)), alkyl acrylate/octylacrylamide copolymer (Amphomer V-42 (AkzoNobel)), alkyl acrylate/diacetone acrylamide copolymer (Placize L-9540B, Placize L-53P, Placize L-9909B, etc. (GOO Chemical Co., Ltd.)), alkyl acrylate/octylacrylamide copolymer (Dermacryl 79 (AkzoNobel)), vinyl acetate/crotonic acid/vinyl neodecanoate terpolymer (RESYN 28-2930 (AkzoNobel)), acrylic acid/acrylamide/ethyl acrylate terpolymer (Ultrahold 8, Ultrahold Strong (BASF)), alkyl acrylate copolymer (Aniset NF-1000, Aniset HS-300, etc. (Osaka Organic Chemical Industry Ltd.)), polyethylene glycol/polypropylene glycol-25/dimethicone/acrylates terpolymer (Luviflex SILK (BASF)), isophorone diisocyanate/dimethylol propionate/(polyoxyethylene/polyoxypropylene) 4,4'-isopropylidene diphenol terpolymer (DynamX (AkzoNobel)), polyacrylate 22 (Luviset Shape (BASF)), vinyl methyl ether/alkyl maleate copolymer (Gantrez A-425, Gantrez ES-225L, Gantrez ES-425L, etc. (ISP Corp.)), crotonic acid/vinyl (C8-12) isoalkyl esters/VA/bis-vinyldimethicone crosspolymer (BELSIL P1101 (Wacker Asahikasei Silicone Co., Ltd.)), and alkyl acrylate/dimethicone copolymer (KP545 (Shin-Etsu Chemical Co., Ltd.)). From the viewpoint of improving the feel of hair after coloring and the feel of use upon application, and also from the viewpoint of imparting excellent hair stylability, it is preferable to use at least one type of resin selected from the group consisting of alkyl acrylate/diacetone acrylamide copolymer, vinyl acetate/crotonic acid/vinyl neodecanoate terpolymer, isophorone diisocyanate/dimethylol propionate/(polyoxyethylene/polyoxypropylene) 4,4'-isopropylidene diphenol terpolymer, vinyl methyl ether/alkyl maleate copolymer, crotonic acid/vinyl (C8-12) isoalkyl esters/VA/bis-vinyldimethicone crosspolymer, and alkyl acrylate/dimethicone copolymer.

Examples of nonionic resins include polyvinylpyrrolidone (Luviskol K17, Luviskol K30, Luviskol K90 (BASF)), vinylpyrrolidone/vinyl acetate copolymer (Luviskol VA73E, Luviskol 37E (BASF)), vinyl methyl ether/alkyl maleate copolymer (Gantrez A-425, Gantrez ES-225, etc. (ISP Corp.)), vinylpyrrolidone/methacrylamide/vinylimidazole terpolymer (Luviset Clear (BASF)), polyvinylcaprolactam (Luviskol Plus (BASF)), polysilicone-28, acrylates/methoxy PEG-23 methacrylate copolymer disclosed in JP 2015-13842A, polysilicone 13, and PEG-12 dimethicone. Among the above, from the viewpoint of imparting excellent slidability between the hair and the sheet upon use and imparting elasticity and resilience to the hair after drying, it is preferable to use at least one type of resin selected from the group consisting of polyvinylpyrrolidone, vinylpyrrolidone/vinyl acetate copolymer, vinyl methyl ether/alkyl maleate copolymer, polysilicone-28, acrylates/methoxy PEG-23 methacrylate copolymer disclosed in JP 2015-13842A, polysilicone 13, and PEG-12 dimethicone.

Examples of amphoteric resins include acrylates/lauryl acrylate/stearyl acrylate/ethylamine oxide methacrylate terpolymer (Diaformer Z651, Diaformer Z712 (Mitsubishi Chemical Corporation)), methacryloyloxyethylcarboxybetaine/alkyl methacrylate copolymer (Yukaformer M75, Yukaformer R205, etc. (Mitsubishi Chemical Corporation), RAM Resin (Osaka Organic Chemical Industry Ltd.)), octylacrylamide/hydroxypropyl acrylate/butylaminoethyl methacrylate terpolymer (Amphomer 28-4910, Amphomer SH-701, Amphomer LV-78, Amphomer LV-47 (AkzoNobel)), octylamide acrylate/hydroxypropyl acrylate/butyl aminoethyl methacrylate terpolymer (Amphomer SH30 (AkzoNobel)), and acrylates/stearyl acrylate/ethylamine oxide methacrylate terpolymer (Diaformer Z-732 (Mitsubishi Chemical Corporation)). Among the above, from the viewpoint of further improving washability of the hair and imparting elasticity and resilience to the hair after drying, it is preferable to use at least one type of resin selected from the group consisting of acrylates/lauryl acrylate/stearyl acrylate/ethylamine oxide methacrylate terpolymer, methacryloyloxyethylcarboxybetaine/alkyl methacrylate copolymer, and octylacrylamide/hydroxypropyl acrylate/butylaminoethyl methacrylate terpolymer.

For the film-forming resin, it is preferable to include at least one type of resin selected from the group consisting of cationic resins, anionic resins, and nonionic resins, and more preferably include at least one type of resin selected from the group consisting of cationic resins and anionic resins. Preferable resins are as described above. For the film-forming resin, one type of the resin described above may be used, or two or more types of resins may be used in combination.

In the hair cosmetic, from the viewpoint of sufficiently fixing the pigment to the hair in an amount sufficient for covering the hair, the content by percentage of the film-forming resin is preferably 5 mass % or greater, more preferably 7 mass % or greater, even more preferably 9 mass % or greater, and preferably 25 mass % or less, more preferably 20 mass % or less, even more preferably 18 mass % or less. In the hair cosmetic, from the viewpoint of covering up the original hair color, regardless of whether the original hair color was black or blond, and developing a vivid color completely different from the original hair color, the content by percentage of the pigment is preferably 0.5 mass % or greater, more preferably 1.0 mass % or greater, even more preferably 1.5 mass % or greater, and preferably 20 mass % or less, more preferably 10 mass % or less, even more preferably 7 mass % or less.

In the hair cosmetic of the invention, from the viewpoint of making it less likely for the color to get removed by the hair rubbing against one another or by being combed after coloring, and suppressing color staining after combing, the mass ratio of the film-forming resin to the pigment ("the mass of the film-forming resin"/"the mass of the pigment") is preferably 0.5 or greater, more preferably 2 or greater, even more preferably 3 or greater. Further, from the viewpoint of suppressing clinging to the fingers and achieving excellent rinseability, the mass ratio is preferably 20 or less, more preferably 10 or less, even more preferably 6 or less.

Liquid Viscosity:

From the viewpoint of easily applying and spreading the solution uniformly, the viscosity of the hair cosmetic is preferably 2500 mPa·s or less, more preferably 2000 mPa·s or less, even more preferably 1500 mPa·s or less. From the viewpoint of suppressing dripping of the hair cosmetic from the retention element, the viscosity is preferably 5 mPa·s or greater, more preferably 10 mPa·s or greater, more preferably 15 mPa·s or greater, even more preferably 20 mPa·s or greater.

The viscosity of the hair cosmetic is measured with a B-type viscometer TVB-10M (from Toki Sangyo Co., Ltd.) by employing the following rotors and rotation speed after rotation at 30° C. for 60 seconds. When the viscosity of the hair cosmetic is up to 10 mPa·s, the rotation speed employed is 30 rpm; when the viscosity is greater than 10 mPa·s to 20 mPa's, the rotation speed is 60 rpm; and when the viscosity is greater than 20 mPa·s, the rotation speed is 30 rpm. Alternatively, when the viscosity of the hair cosmetic is up to 10 mPa·s, the rotor used is L/Adp; when the viscosity is greater than 10 mPa·s to 200 mPa·s, the rotor is M1; when the viscosity is greater than 200 mPa·s to 1,000 mPa·s, the rotor is M2; and when the viscosity is greater than 1,000 mPa·s, the rotor is M3.

Figure 9:
FIG. 9 illustrates schematic diagrams illustrating how the hair on one's head is treated by using the hair treatment tool illustrated in FIG. 1 or FIG. 3.
Figure 9:
Figure 9:
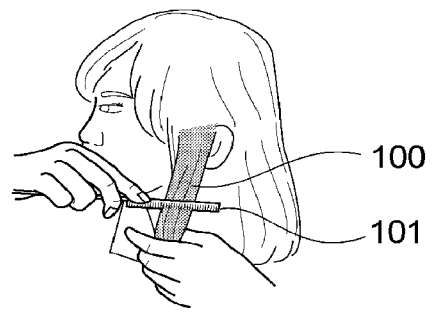
Figure 9:

A hair treatment method using the hair treatment tool 1 illustrated in FIG. 3 is described below, taking an example of treating hair with a hair cosmetic. FIG. 9 illustrates a method for treating hair with the hair treatment tool 1. As illustrated in FIG. 9(*a*), it is preferable that, in cases where a handler handling the hair treatment tool 1 wants to treat (coat) a portion of hair neatly, the handler creates a hair strand 100 in advance by separating a portion of the hair on one's head, but the present usage method can be performed without creating a hair strand 100. Before or after separating a hair strand 100, the packaging 2 is torn (opened), to expose the fiber structure member 5 of the hair treatment tool 1. In cases where another person is helping, separating of a portion of hair can be performed simultaneously with the opening of the packaging 2.

Next, the separated hair strand 100 is sandwiched by the fiber structure member 5 of the opened hair treatment tool 1. More specifically, the hair is sandwiched between the gripping piece 30 and the main body portion 40 which are created by tearing the packaging 2, and the fiber structure member 5, which is supported by the gripping piece 30 and the main body portion 40, is brought into contact with the hair. In the hair treatment tool 1, the fiber structure member 5 is folded in two in a manner that the surface thereof faces inward, and the hair strand 100 is sandwiched between the fiber structure member 5 having been folded in two. Then, while sandwiching the hair strand 100 between the fiber structure member 5, the hair treatment tool 1 is moved in the length direction of the hair strand 100 (see FIG. 9(*b*)). The hair strand 100 is a portion of the hair, and the length direction of the hair strand 100 is the same as the direction of orientation of the hair constituting the hair strand 100. With this operation method, the task of applying the hair cosmetic to the hair is easy, because the handler can intuitively grasp the position of the fiber structure member 5.

The position of the hair to be sandwiched by the hair treatment tool 1 may be the middle of the hair strand 100, i.e., the hair treatment tool 1 may sandwich a portion between the root and the tip end of the hair strand 100. Alternatively, the hair treatment tool 1 may sandwich the root portion of the hair strand 100, or the tip end portion of the hair strand 100. In either case, it is preferable to slide the hair treatment tool 1 sandwiching the hair strand toward the tip end of the hair. This is because, in this way, it is possible to apply the hair cosmetic more uniformly to the hair strand.

From the viewpoint of controlling the dischargibility of the hair cosmetic in a balanced manner, it is preferable that the operation of sliding the hair treatment tool 1, while sandwiching the hair with the hair treatment tool 1, is performed while pressurizing the fiber structure member 5 with the fingers.

The operation of sliding the hair treatment tool 1 from the initially sandwiched section toward the tip end of the hair may be performed only once for each section to be treated, and in many cases, uniform application is possible with a single operation. It is, however, possible to perform the operation a plurality of times, if desired.

Then, the applied hair cosmetic is dried. At this time, in cases where it is desired to provide the hair with a natural texture, it is preferable to comb the hair strand with a known comb 101, as illustrated in FIG. 9(*c*), when the hair is semi-dry. A hair brush or hand combing may be used instead of a comb. Examples of methods for drying the applied hair cosmetic include drying with warm air using a blowing device such as a hairdryer, drying with cool air using a blowing device such as a hairdryer, and natural drying; natural drying is preferred.

The aforementioned operation may be performed repeatedly in sections, among all the hair on one's head, where treatment with the hair cosmetic is desired. FIG. 9(*d*) illustrates a colored state after treating the hair on the sides with a temporary hair colorant employed as a hair cosmetic, and then treating a portion of the bangs in the same way.

Further, the hair after being treated with the hair treatment tool 1 may further be provided with a desired shape, such as curls. In this case, it is preferable that the hair after being treated with the hair treatment tool 1 is in a half-dried state or a dried state. Upon shaping the hair, the hair may be heated, or shaping may be performed without heating; it is, however, preferable to perform shaping with a heating tool. Examples of heating tools include hairdryers, hot curlers, heaters, hair irons, and curling tongs. Various conventionally known methods may be used for shaping the hair into a desired shape.

With the hair treatment tool and the hair treatment method of the present invention, for example, the person who wants his/her hair to be treated can be the handler and can easily perform a desired hair treatment on a portion of his/her hair as described above. For example, the following effects (a) to (d) may be achieved.

(a) The fiber structure member 5 retaining the hair cosmetic is fixed to the liquid-impermeable sheet 3, and the user can perform hair treatment by indirectly holding the fiber structure member 5 through the liquid-impermeable sheet 3. Thus, it is possible to prevent the hair cosmetic from adhering to the fingers and the palm, and prevent problems caused by the adhesion of the hair cosmetic to the skin—for example, in cases where the hair cosmetic is a temporary hair colorant, it is possible to prevent the fingers from getting colored by the temporary hair colorant.

(b) A suitable amount of the hair cosmetic can be retained in the fiber structure member in advance. Thus, even in cases where an ordinary consumer performs the treatment, it is possible to prevent liquid dripping and adhesion of the liquid to unwanted places, and also prevent the hair from getting rough and stiff by excessive application. Further, even in cases where only a portion of the hair is to be subjected to hair treatment, such as coloring, it is possible to appropriately treat only the desired portion.

(c) The hair cosmetic can be supplied gradually by performing treatment by pressing the hair cosmetic, which is retained by the fiber structure member, against the hair. Thus, it is possible to apply the hair cosmetic uniformly over a wide area in the length direction of the hair, compared to cases where the hair is treated by spraying the hair cosmetic or by applying the hair cosmetic to the hair with a brush, a hairbrush, a sponge, or the like. It is also easy to apply the hair cosmetic uniformly not only to the front side of the separated hair strand, but also to the back side. In this way, unevenness in coloring is less likely to occur, compared to cases where a temporary hair colorant, as the hair cosmetic, is applied with a mascara brush.

(d) While performing application, it is easy to perceive, by the sense of touch with the fingers, the section where the treatment is being performed. Thus, the hair cosmetic can be applied easily to the section that the user wants to treat, whereas the hair cosmetic can be prevented from adhering to sections that the user does not want to treat.

The hair may be hair other than that on one's head, and may be the eyebrows or eyelashes, for example. The hair may be hair of mammals other than human beings, and for example, may be hair/fur of pets, such as dogs, cats, rabbits, and goats.

The hair treatment method of the invention may be performed by a handler performing the method on his/her hair as illustrated in FIG. 9, or may be performed by a professional, such as a hairdresser, performing the method on another person's hair.

The scope of the invention is not limited to the foregoing embodiments. Further, the invention also discloses the following hair treatment methods and hair treatment tools.

{1}

A hair treatment method for treating hair by using a hair treatment tool comprising a fiber structure member and a liquid-impermeable sheet to which the fiber structure member is fixed, the fiber structure member retaining a hair cosmetic that includes a pigment and a film-forming resin, the fiber structure member being sealed in a packaging, the method comprising steps 1 and 2 below:

step 1: exposing a surface of the fiber structure member of the hair treatment tool; and step 2: bringing the fiber structure member, whose surface has been exposed in step 1, into contact with hair, and in this state, moving the fiber structure member in a direction of orientation of the hair.

{2}

The hair treatment method as set forth in clause {1}, wherein the fiber structure member is fixed to the liquid-impermeable sheet by ultrasonic sealing and/or heat sealing.

{3}

The hair treatment method as set forth in clause {1} or {2}, wherein the fiber structure member is arranged on a surface of the liquid-impermeable sheet in a manner that the surface of the liquid-impermeable sheet to which the fiber structure member is fixed opposes a surface of the fiber structure member opposite from the surface that comes into contact with the hair.

{4}

The hair treatment method as set forth in any one of clauses {1} to {3}, wherein the fiber structure member is arranged in a state in which the fiber structure member spans a folding portion at which the liquid-impermeable sheet is folded in two, in a manner that the surfaces of the fiber structure member that come into contact with the hair face one another.

{5}

The hair treatment method as set forth in any one of clauses {1} to {4}, wherein the fiber structure member is fixed to the liquid-impermeable sheet at a plurality of sections separated from one another in the lateral direction or the longitudinal direction.

{6}

The hair treatment method as set forth in any one of clauses {1} to {5}, wherein, on the surface side of the fiber structure member, projections and depressions are formed in a plurality of rows in a manner extending in one direction within the plane.

{7}

The hair treatment method as set forth in any one of clauses {1} to {6}, wherein: in the hair treatment tool, a sheet that forms one surface of the packaging is tearable in a manner that creates a gripping piece and a main body portion to which one end of the gripping piece is connected; and, in an opened state in which the packaging has been torn, the fiber structure member is located on an inner surface of each of the gripping piece and the main body portion, the respective inner surface being the surface that had been facing toward inside of the packaging.

{8}

The hair treatment method as set forth in clause {7}, wherein the fiber structure member is fixed on the inner surface of the gripping piece.

{9}

The hair treatment method as set forth in clause {7} or {8}, wherein the fiber structure member is fixed on the inner surface of the main body portion.

{10}

The hair treatment method as set forth in any one of clauses {7} to {9}, wherein the sheet has tear rectilinearity in the tearing direction.

{11}

The hair treatment method as set forth in any one of clauses {7} to {10}, wherein: a portion of the fiber structure member located on the main body portion and a portion of the fiber structure member located on the gripping piece are continuous; and the fiber structure member is contained in the packaging in a folded state in a manner that a folding portion located between the two portions is located on the connecting portion side where the gripping piece and the main body portion are connected.

{12}

The hair treatment method as set forth in any one of clauses {7} to {11}, wherein, in the opened state, the portion of the fiber structure member located on the main body portion and the portion thereof located on the gripping piece have the same area.

{13}

The hair treatment method as set forth in any one of clauses {7} to {12}, wherein the main body portion has a pocket portion on one side, or pocket portions on both sides, in a direction intersecting with the tearing direction of the sheet.

{14}

The hair treatment method as set forth in any one of clauses {7} to {13}, wherein: the packaging has at least one fixing seal portion where the sheet is joined with an opposing sheet opposing the sheet, the fixing seal portion being provided on one side, or the fixing seal portions being provided on both sides, in a direction intersecting with the tearing direction of the sheet; and, in the direction intersecting with the tearing direction, the tearing position of the sheet is located more toward the central side than the fixing seal portion(s).

{15}

The hair treatment method as set forth in any one of clauses {7} to {14}, wherein: the packaging has an opening seal portion where the sheet is joined with an opposing sheet opposing the sheet, the opening seal portion being provided more toward the starting end side than the central position in the tearing direction of the sheet; and the sheets at the opening seal portion are peeled apart when the sheet is torn.

{16}

The hair treatment method as set forth in any one of clauses {1} to {15}, wherein, in the step 2, the fiber structure member is folded in two in a manner that the surface thereof faces inward, and the fiber structure member is moved in the direction of orientation of the hair in a state where a hair strand is sandwiched between the fiber structure member having been folded in two.

{17}

The hair treatment method as set forth in any one of clauses {7} to {16}, wherein the hair cosmetic is applied to the hair by sliding the hair treatment tool while sandwiching the hair between the gripping piece and the main body portion of the hair treatment tool.

{18}

The hair treatment method as set forth in any one of clauses {1} to {17}, wherein the hair cosmetic includes preferably 70 mass % or greater, more preferably 75 mass % or greater, more preferably 80 mass % or greater, of an organic solvent having a boiling point of from 50° C. to 260° C., and the content by percentage of water is preferably 10 mass % or less.

{19}

The hair treatment method as set forth in any one of clauses {1} to {18}, wherein the hair cosmetic is a temporary hair colorant.

{20}

The hair treatment method as set forth in any one of clauses {1} to {19}, wherein the hair cosmetic has a viscosity at 30° C. of preferably 2500 mPa·s or less, more preferably 2000 mPa·s or less, even more preferably 1500 mPa·s or less, and preferably 5 mPa·s or greater, more preferably 10 mPa·s or greater, more preferably 15 mPa·s or greater, even more preferably 20 mPa·s or greater.

{21}

The hair treatment method as set forth in any one of clauses {1} to {20}, wherein the fiber structure member has a structure formed by layering a plurality of layers.

{22}

The hair treatment method as set forth in clause {21}, wherein the fiber structure member includes: an application layer including a surface layer constituting the surface that contacts the hair; and a lower layer arranged more toward the liquid-impermeable sheet side than the application layer.

{23}

The hair treatment method as set forth in clause {22}, wherein the content by percentage of cellulosic fiber in all constituent fibers of the application layer is different from the content by percentage of cellulosic fiber in all constituent fibers of the lower layer.

{24}

The hair treatment method as set forth in clause {22} or {23}, wherein the lower layer is constituted by a nonwoven fabric having a higher impregnation rate than the application layer, the impregnation rate being a rate of the mass after impregnation to the mass before impregnation.

{25}

The hair treatment method as set forth in clause {24}, wherein the content by percentage of cellulosic fiber in all constituent fibers of the application layer is lower than the content by percentage of cellulosic fiber in all constituent fibers of the lower layer.

{26}

The hair treatment method as set forth in clause {24} or {25}, wherein the content by percentage of cellulosic fiber in the lower layer with respect to the mass of all constituent fibers in the lower layer is preferably 60 mass % or greater, and preferably 95 mass % or less, more preferably 90 mass % or less, and preferably from 60 to 95 mass %, more preferably from 60 to 90 mass %.

{27}

The hair treatment method as set forth in clause {24} or {23}, wherein the application layer is constituted by a nonwoven fabric having a higher impregnation rate than the lower layer, the impregnation rate being a rate of the mass after impregnation to the mass before impregnation.

{28}

The hair treatment method as set forth in clause {27}, wherein the content by percentage of cellulosic fiber in all constituent fibers of the application layer is higher than the content by percentage of cellulosic fiber in all constituent fibers of the lower layer.

{29}

The hair treatment method as set forth in clause {27} or {28}, wherein the content by percentage of cellulosic fiber in the application layer with respect to the mass of all constituent fibers in the application layer is preferably 60 mass % or greater, more preferably greater than 60 mass %, and preferably 95 mass % or less, more preferably 90 mass % or less, and preferably from 60 to 95 mass %, more preferably greater than 60 mass % to 95 mass % or less, even more preferably from 60 to 90 mass %.

{30}
The hair treatment method as set forth in any one of clauses {23} to {29}, wherein the ratio d2/d1 of the thickness d2 of the lower layer to the thickness d1 of the application layer is preferably 0.7 or greater, more preferably 0.9 or greater, more preferably 1.0 or greater, even more preferably 1.3 or greater, and preferably 15 or less, more preferably 10 or less, even more preferably 7.5 or less, and preferably from 0.7 to 15, more preferably from 0.9 to 15, more preferably from 1.0 to 10, even more preferably from 1.3 to 7.5.

{31}
The hair treatment method as set forth in any one of clauses {1} to {20}, wherein at least the surface side of the fiber structure member includes preferably 5 mass % or greater, more preferably 10 mass % or greater, and preferably 60 mass % or less, more preferably 50 mass % or less, and preferably from 5 to 60 mass %, more preferably from 10 to 50 mass %, of cellulosic fiber.

{32}
The hair treatment method as set forth in any one of clauses {1} to {31}, wherein an entirety or a portion of the packaging is formed by the liquid-impermeable sheet.

{33}
The hair treatment method as set forth in any one of clauses {1} to {32}, wherein the fiber structure member is contained in a folded state in the packaging.

{34}
The hair treatment method as set forth in any one of clauses {1} to {33}, wherein the film-forming resin includes at least one type of film-forming resin selected from the group consisting of cationic resins, anionic resins, and nonionic resins.

{35}
The hair treatment method as set forth in clause {34}, wherein the nonionic resin is at least one type of resin selected from the group consisting of polyvinylpyrrolidone, vinylpyrrolidone/vinyl acetate copolymer, vinyl methyl ether/alkyl maleate copolymer, polysilicone-28, acrylates/methoxy PEG-23 methacrylate copolymer, polysilicone 13, and PEG-12 dimethicone.

{36}
The hair treatment method as set forth in any one of clauses {1} to {35}, wherein the film-forming resin includes at least one type of film-forming resin selected from the group consisting of cationic resins and anionic resins.

{37}
The hair treatment method as set forth in any one of clauses {34} to {36}, wherein the cationic resin is at least one type of resin selected from the group consisting of dimethyldiallylammonium chloride/acrylamide copolymer, vinylpyrrolidone/N,N-dimethylaminoethyl methacrylate copolymer diethyl sulfate, N,N-dimethyl aminoethyl methacrylate diethyl sulfate/N,N-dimethylacrylamide/polyethylene glycol dimethacrylate terpolymer, and ammonium-modified hydroxyethyl cellulose.

{38}
The hair treatment method as set forth in any one of clauses {34} to {37}, wherein the anionic resin is at least one type of resin selected from the group consisting of alkyl acrylate/diacetone acrylamide copolymer, vinyl acetate/crotonic acid/vinyl neodecanoate terpolymer, isophorone diisocyanate/dimethylol propionate/(polyoxyethylene/polyoxypropylene) 4,4'-isopropylidene diphenol terpolymer, vinyl methyl ether/alkyl maleate copolymer, crotonic acid/vinyl (C8-12) isoalkyl esters/VA/bis-vinyl dimethicone crosspolymer, and alkyl acrylate/dimethicone copolymer.

{39}
The hair treatment method as set forth in any one of clauses {1} to {38}, wherein the content of the pigment in the hair cosmetic is preferably 0.5 mass % or greater, more preferably 1 mass % or greater, even more preferably 1.5 mass % or greater, and preferably 20 mass % or less, more preferably 10 mass % or less, even more preferably 7 mass % or less.

{40}
The hair treatment method as set forth in any one of clauses {1} to {39}, wherein the content of the film-forming resin in the hair cosmetic is preferably 5 mass % or greater, more preferably 7 mass % or greater, even more preferably 9 mass % or greater, and preferably 25 mass % or less, more preferably 20 mass % or less, even more preferably 18 mass % or less.

{41}
The hair treatment method as set forth in any one of clauses {1} to {40}, wherein the mass ratio of the film-forming resin to the pigment in the hair cosmetic ("the mass of the film-forming resin"/"the mass of the pigment") is preferably 0.5 or greater, more preferably 2 or greater, even more preferably 3 or greater, and preferably 20 or less, more preferably 10 or less, even more preferably 6 or less.

{42}
A hair treatment method for treating hair by using a hair treatment tool comprising a fiber structure member and a liquid-impermeable sheet to which the fiber structure member is fixed, the fiber structure member retaining a hair cosmetic that includes a pigment and a film-forming resin, the fiber structure member being sealed in a packaging, wherein:
  the hair cosmetic is a temporary hair colorant;
  the hair cosmetic includes preferably 70 mass % or greater of an organic solvent having a boiling point of from 50° C. to 260° C., and the content by percentage of water is preferably 10 mass % or less;
  the hair cosmetic has a viscosity of preferably 2500 mPa·s or less at 30° C.;
  the content of the pigment in the hair cosmetic is from 1.0 to 10 mass %;
  the content of the film-forming resin in the hair cosmetic is from 7 to 20 mass %;
  the film-forming resin includes at least one type of film-forming resin selected from the group consisting of cationic resins and anionic resins;
  the cationic resin is at least one type of resin selected from the group consisting of dimethyldiallylammonium chloride/acrylamide copolymer, vinylpyrrolidone/N,N-dimethylaminoethyl methacrylate copolymer diethyl sulfate, N,N-dimethylaminoethyl methacrylate diethyl sulfate/N,N-dimethylacrylamide/polyethylene glycol dimethacrylate terpolymer, and ammonium-modified hydroxyethyl cellulose;
  the anionic resin is at least one type of resin selected from the group consisting of alkyl acrylate/diacetone acrylamide copolymer, vinyl acetate/crotonic acid/vinyl neodecanoate terpolymer, isophorone diisocyanate/dimethylol propionate/(polyoxyethylene/polyoxypropylene) 4,4'-isopropylidene diphenol terpolymer, vinyl methyl ether/alkyl maleate copolymer, crotonic acid/vinyl (C8-12) isoalkyl esters/VA/bisvinyl dimethicone crosspolymer, and alkyl acrylate/dimethicone copolymer;

the fiber structure member includes: an application layer including a surface layer constituting a surface that contacts the hair; and a lower layer arranged more toward the liquid-impermeable sheet side than the application layer;

each of the application layer and the lower layer is constituted by a single layer, or by a layered structure formed by layering a plurality of sheets each having the same impregnation rate of the hair cosmetic;

the content by percentage of cellulosic fiber in the application layer with respect to the mass of all constituent fibers in the application layer is from 60 to 95 mass %; and the hair treatment method comprises steps 1 and 2 below:

step 1: exposing a surface of the fiber structure member of the hair treatment tool; and step 2: folding the fiber structure member, whose surface has been exposed in step 1, in two in a manner that the surface thereof faces inward, and, in a state where the fiber structure member is in contact with hair by sandwiching a hair strand between the fiber structure member having been folded in two, moving the fiber structure member in the direction of orientation of the hair.

{43}

A hair treatment method for treating hair by using a hair treatment tool comprising a fiber structure member and a liquid-impermeable sheet to which the fiber structure member is fixed, the fiber structure member retaining a hair cosmetic that includes a pigment and a film-forming resin, the fiber structure member being sealed in a packaging, wherein:

the hair cosmetic is a temporary hair colorant;

the hair cosmetic includes preferably 70 mass % or greater of an organic solvent having a boiling point of from 50° C. to 260° C., and the content by percentage of water is preferably 10 mass % or less;

the hair cosmetic has a viscosity of preferably 2500 mPa·s or less at 30° C.;

the content of the pigment in the hair cosmetic is from 1.0 to 10 mass %;

the content of the film-forming resin in the hair cosmetic is from 7 to 20 mass %;

the film-forming resin includes at least one type of film-forming resin selected from the group consisting of cationic resins and anionic resins;

the cationic resin is at least one type of resin selected from the group consisting of dimethyldiallylammonium chloride/acrylamide copolymer, vinylpyrrolidone/N,N-dimethylaminoethyl methacrylate copolymer diethyl sulfate, N,N-dimethylaminoethyl methacrylate diethyl sulfate/N,N-dimethylacrylamide/polyethylene glycol dimethacrylate terpolymer, and ammonium-modified hydroxyethyl cellulose;

the anionic resin is at least one type of resin selected from the group consisting of alkyl acrylate/diacetone acrylamide copolymer, vinyl acetate/crotonic acid/vinyl neodecanoate terpolymer, isophorone diisocyanate/dimethylol propionate/(polyoxyethylene/polyoxypropylene) 4,4'-isopropylidene diphenol terpolymer, vinyl methyl ether/alkyl maleate copolymer, crotonic acid/vinyl (C8-12) isoalkyl esters/VA/bisvinyl dimethicone crosspolymer, and alkyl acrylate/dimethicone copolymer;

the fiber structure member includes: an application layer including a surface layer constituting a surface that contacts the hair; and a lower layer arranged more toward the liquid-impermeable sheet side than the application layer;

each of the application layer and the lower layer is constituted by a single layer, or by a layered structure formed by layering a plurality of sheets each having the same impregnation rate of the hair cosmetic;

the content by percentage of cellulosic fiber in the lower layer with respect to the mass of all constituent fibers in the lower layer is from 60 to 95 mass %; and the hair treatment method comprises steps 1 and 2 below:

step 1: exposing a surface of the fiber structure member of the hair treatment tool; and step 2: folding the fiber structure member, whose surface has been exposed in step 1, in two in a manner that the surface thereof faces inward, and, in a state where the fiber structure member is in contact with hair by sandwiching a hair strand between the fiber structure member having been folded in two, moving the fiber structure member in the direction of orientation of the hair.

{44}

A hair treatment tool comprising:

a fiber structure member; and a liquid-impermeable sheet to which the fiber structure member is fixed, wherein the fiber structure member retains a hair cosmetic that includes a pigment and a film-forming resin, and the fiber structure member is sealed in a packaging.

{45}

The hair treatment tool as set forth in clause {44}, wherein the fiber structure member is fixed to the liquid-impermeable sheet by ultrasonic sealing and/or heat sealing.

{46}

The hair treatment tool as set forth in clause {44} or {45}, wherein the fiber structure member is arranged on a surface of the liquid-impermeable sheet in a manner that the surface of the liquid-impermeable sheet to which the fiber structure member is fixed opposes a surface of the fiber structure member opposite from the surface that comes into contact with the hair.

{47}

The hair treatment tool as set forth in any one of clauses {44} to {46}, wherein the fiber structure member is arranged in a state in which the fiber structure member spans a folding portion at which the liquid-impermeable sheet is folded in two, in a manner that the surfaces of the fiber structure member that come into contact with the hair face one another.

{48}

The hair treatment tool as set forth in any one of clauses {44} to {47}, wherein the fiber structure member is fixed to the liquid-impermeable sheet at a plurality of sections separated from one another in the lateral direction or the longitudinal direction.

{49}

The hair treatment tool as set forth in any one of clauses {44} to {48}, wherein, on the surface side of the fiber structure member, projections and depressions are formed in a plurality of rows in a manner extending in one direction within the plane.

{50}

The hair treatment tool as set forth in any one of clauses {44} to {49}, wherein: in the hair treatment tool, a sheet that forms one surface of the packaging is tearable in a manner that creates a gripping piece and a main body portion to which one end of the gripping piece is connected; and, in an opened state in which the packaging has been torn, the fiber structure member is located on an inner surface of each of the gripping piece and the main body portion, the respective inner surface being the surface that had been facing toward inside of the packaging.

{51}

The hair treatment tool as set forth in clause {50}, wherein the fiber structure member is fixed on the inner surface of the gripping piece.

{52}

The hair treatment tool as set forth in clause {50} or {51}, wherein the fiber structure member is fixed on the inner surface of the main body portion.

{53}

The hair treatment tool as set forth in any one of clauses {50} to {52}, wherein the sheet has tear rectilinearity in the tearing direction.

{54}

The hair treatment tool as set forth in any one of clauses {48} to {51}, wherein: a portion of the fiber structure member located on the main body portion and a portion of the fiber structure member located on the gripping piece are continuous; and the fiber structure member is contained in the packaging in a folded state in a manner that a folding portion located between the two portions is located on the connecting portion side where the gripping piece and the main body portion are connected.

{55}

The hair treatment tool as set forth in any one of clauses {50} to {54}, wherein, in the opened state, the portion of the fiber structure member located on the main body portion and the portion thereof located on the gripping piece have the same area.

{56}

The hair treatment tool as set forth in any one of clauses {50} to {55}, wherein: the packaging has at least one fixing seal portion where the sheet is joined with an opposing sheet opposing the sheet, the fixing seal portion being provided on one side, or the fixing seal portions being provided on both sides, in a direction intersecting with the tearing direction of the sheet; and, in the direction intersecting with the tearing direction, the tearing position of the sheet is located more toward the central side than the fixing seal portion(s).

{57}

The hair treatment tool as set forth in any one of clauses {50} to {56}, wherein: the packaging has an opening seal portion where the sheet is joined with an opposing sheet opposing the sheet, the opening seal portion being provided more toward the starting end side than the central position in the tearing direction of the sheet; and the sheets at the opening seal portion are peeled apart when the sheet is torn.

{58}

The hair treatment tool as set forth in any one of clauses {44} to {57}, wherein, in the step 2, the fiber structure member is folded in two in a manner that the surface thereof faces inward, and the fiber structure member is moved in the direction of orientation of the hair in a state where a hair strand is sandwiched between the fiber structure member having been folded in two.

{59}

The hair treatment tool as set forth in any one of clauses {50} to {58}, wherein the hair cosmetic is applied to the hair by sliding the hair treatment tool while sandwiching the hair between the gripping piece and the main body portion of the hair treatment tool.

{60}

The hair treatment tool as set forth in any one of clauses {44} to {59}, wherein the hair cosmetic includes preferably 70 mass % or greater, more preferably 75 mass % or greater, more preferably 80 mass % or greater, of an organic solvent having a boiling point of from 50° C. to 260° C., and the content by percentage of water is preferably 10 mass % or less.

{61}

The hair treatment tool as set forth in any one of clauses {44} to {60}, wherein the hair cosmetic is a temporary hair colorant.

{62}

The hair treatment tool as set forth in any one of clauses {44} to {61}, wherein the hair cosmetic has a viscosity at 30° C. of preferably 2500 mPa·s or less, more preferably 2000 mPa·s or less, even more preferably 1500 mPa·s or less, and preferably 5 mPa·s or greater, more preferably 10 mPa·s or greater, more preferably 15 mPa·s or greater, even more preferably 20 mPa·s or greater.

{63}

The hair treatment tool as set forth in any one of clauses {44} to {62}, wherein the fiber structure member has a structure formed by layering a plurality of layers.

{64}

The hair treatment tool as set forth in clause {63}, wherein the fiber structure member includes: an application layer including a surface layer constituting the surface that contacts the hair; and a lower layer arranged more toward the liquid-impermeable sheet side than the application layer.

{65}

The hair treatment tool as set forth in clause {64}, wherein the content by percentage of cellulosic fiber in all constituent fibers of the application layer is different from the content by percentage of cellulosic fiber in all constituent fibers of the lower layer.

{66}

The hair treatment tool as set forth in clause {64} or {65}, wherein the lower layer is constituted by a nonwoven fabric having a higher impregnation rate than the application layer, the impregnation rate being a rate of the mass after impregnation to the mass before impregnation.

{67}

The hair treatment tool as set forth in clause {66}, wherein the content by percentage of cellulosic fiber in all constituent fibers of the application layer is lower than the content by percentage of cellulosic fiber in all constituent fibers of the lower layer.

{68}

The hair treatment tool as set forth in clause {66} or {67}, wherein the content by percentage of cellulosic fiber in the lower layer with respect to the mass of all constituent fibers in the lower layer is preferably 60 mass % or greater, and preferably 95 mass % or less, more preferably 90 mass % or less, and preferably from 60 to 95 mass %, more preferably from 60 to 90 mass %.

{69}

The hair treatment tool as set forth in clause {64} or {65}, wherein the application layer is constituted by a nonwoven fabric having a higher impregnation rate than the lower layer, the impregnation rate being a rate of the mass after impregnation to the mass before impregnation.

{70}

The hair treatment tool as set forth in clause {69}, wherein the content by percentage of cellulosic fiber in all constituent fibers of the application layer is higher than the content by percentage of cellulosic fiber in all constituent fibers of the lower layer.

{71}

The hair treatment tool as set forth in clause {69} or {70}, wherein the content by percentage of cellulosic fiber in the application layer with respect to the mass of all constituent fibers in the application layer is preferably 60 mass % or greater, more preferably greater than 60 mass %, and preferably 95 mass % or less, more preferably 90 mass % or less, and preferably from 60 to 95 mass %, more preferably greater than 60 mass % to 95 mass % or less, even more preferably from 60 to 90 mass %.

{72}
The hair treatment tool as set forth in any one of clauses {65} to {71}, wherein the ratio d2/d1 of the thickness d2 of the lower layer to the thickness d1 of the application layer is preferably 0.7 or greater, more preferably 0.9 or greater, more preferably 1.0 or greater, even more preferably 1.3 or greater, and preferably 15 or less, more preferably 10 or less, even more preferably 7.5 or less, and preferably from 0.7 to 15, more preferably from 0.9 to 15, more preferably from 1.0 to 10, even more preferably from 1.3 to 7.5.

{73}
The hair treatment tool as set forth in any one of clauses {44} to {62}, wherein at least the surface side of the fiber structure member includes preferably 5 mass % or greater, more preferably 10 mass % or greater, and preferably 60 mass % or less, more preferably 50 mass % or less, and preferably from 5 to 60 mass %, more preferably from 10 to 50 mass %, of cellulosic fiber.

{74}
The hair treatment tool as set forth in any one of clauses {44} to {73}, wherein an entirety or a portion of the packaging is formed by the liquid-impermeable sheet.

{75}
The hair treatment tool as set forth in any one of clauses {44} to {74}, wherein the fiber structure member is contained in a folded state in the packaging.

{76}
The hair treatment tool as set forth in any one of clauses {44} to {75}, wherein the film-forming resin includes at least one type of film-forming resin selected from the group consisting of cationic resins, anionic resins, and nonionic resins.

{77}
The hair treatment tool as set forth in clause {76}, wherein the nonionic resin is at least one type of resin selected from the group consisting of polyvinylpyrrolidone, vinylpyrrolidone/vinyl acetate copolymer, vinyl methyl ether/alkyl maleate copolymer, polysilicone-28, acrylates/methoxy PEG-23 methacrylate copolymer, polysilicone 13, and PEG-12 dimethicone.

{78}
The hair treatment tool as set forth in any one of clauses {44} to {75}, wherein the film-forming resin includes at least one type of film-forming resin selected from the group consisting of cationic resins and anionic resins.

{79}
The hair treatment tool as set forth in any one of clauses {76} to {78}, wherein the cationic resin is at least one type of resin selected from the group consisting of dimethyldiallylammonium chloride/acrylamide copolymer, vinylpyrrolidone/N,N-dimethylaminoethyl methacrylate copolymer diethyl sulfate, N,N-dimethylaminoethyl methacrylate diethyl sulfate/N,N-dimethylacrylamide/polyethylene glycol dimethacrylate terpolymer, and ammonium-modified hydroxyethyl cellulose.

{80}
The hair treatment tool as set forth in any one of clauses {76} to {79}, wherein the anionic resin is at least one type of resin selected from the group consisting of alkyl acrylate/diacetone acrylamide copolymer, vinyl acetate/crotonic acid/vinyl neodecanoate terpolymer, isophorone diisocyanate/dimethylol propionate/(polyoxyethylene/polyoxypropylene) 4,4'-isopropylidene diphenol terpolymer, vinyl methyl ether/alkyl maleate copolymer, crotonic acid/vinyl (C8-12) isoalkyl esters/VA/bis-vinyl dimethicone crosspolymer, and alkyl acrylate/dimethicone copolymer.

{81}
The hair treatment tool as set forth in any one of clauses {44} to {80}, wherein the content of the pigment in the hair cosmetic is preferably 0.5 mass % or greater, more preferably 1 mass % or greater, even more preferably 1.5 mass % or greater, and preferably 20 mass % or less, more preferably 10 mass % or less, even more preferably 7 mass % or less.

{82}
The hair treatment tool as set forth in any one of clauses {44} to {81}, wherein the content of the film-forming resin in the hair cosmetic is preferably 5 mass % or greater, more preferably 7 mass % or greater, even more preferably 9 mass % or greater, and preferably 25 mass % or less, more preferably 20 mass % or less, even more preferably 18 mass % or less.

{83}
The hair treatment tool as set forth in any one of clauses {44} to {82}, wherein the mass ratio of the film-forming resin to the pigment in the hair cosmetic ("the mass of the film-forming resin"/"the mass of the pigment") is preferably 0.5 or greater, more preferably 2 or greater, even more preferably 3 or greater, and preferably 20 or less, more preferably 10 or less, even more preferably 6 or less.

EXAMPLES

The invention is described in further detail below according to Examples thereof. The invention, however, is not limited to these Examples. It should be noted that "%" refers to mass %, unless specifically stated otherwise.

Example 1

Fiber material including 22% of rayon fiber (fineness: 1.7 dtex; fiber diameter: 12 µm; fiber length: 5 mm), 18% of PET fiber (fineness: 1.7 dtex; fiber diameter: 12.5 µm; fiber length: 10 mm), 50% of PP/PE fiber (core-sheath conjugate fiber; fineness: 2.2 dtex; fiber diameter: 17.5 µm; fiber length: 10 mm), and 10% of PVA fiber (fineness: 1.1 dtex; fiber diameter: 10 µm; fiber length: 3 mm) was subjected to a wet sheet-forming method, to obtain a wet-formed sheet A (nonwoven fabric A) having a basis weight of 45 g/m$^2$.

Fiber material including 70% of rayon fiber (fineness: 1.7 dtex; fiber diameter: 12 µm; fiber length: 40 mm) and 30% of PP/PE fiber (core-sheath conjugate fiber; fineness: 2.2 dtex; fiber diameter: 17.5 µm; fiber length: 51 mm) was subjected to a carding machine to manufacture a carding web, and a water jet stream was applied to the web, to obtain a spun-laced nonwoven fabric C having a basis weight of 60 g/m$^2$.

The obtained wet-formed sheet A and spun-laced nonwoven fabric C were used to obtain a laminate (fiber structure member) having a rectangular planar shape and including a total of five layers, including an application layer constituted by two layers of the wet-formed sheets A and a lower layer constituted by three layers of the spun-laced nonwoven fabrics C. The five-layered laminate was placed on a liquid-impermeable sheet constituted by an aluminum-evaporated thermoplastic resin film prepared separately, and the laminate and the sheet, which included a total of six layers, were joined together by fusion bonding at a plurality of sections separated from one another in the longitudinal direction and the lateral direction as illustrated in FIG. 1, to obtain a hair treatment tool of Example 1.

In the hair treatment tool of Example 1, the fiber structure member constituted by the laminate including a total of five layers had a planar-view shape of a 3-by-4-cm rectangle and had a basis weight of 270 g/m². Further, the surface—i.e., the surface that comes into contact with hair—of the fiber structure member was provided with a plurality of depressions according to the pattern illustrated in FIG. 7(c). This fiber structure member was arranged in a central portion of a 6-by-8-cm rectangular liquid-impermeable sheet and was partially fixed to the liquid-impermeable sheet by fusion bonding.

Examples 2 to 12

Fiber structure members each having a 3-by-4-cm rectangular shape were obtained, respectively constituted by laminates each obtained by layering the nonwoven fabrics A to E shown in Table 1 in order from the application layer to the lower layer as shown in Table 4 and according to the number of layers shown in Table 4. Table 1 shows the fiber composition and basis weight of each of the nonwoven fabrics A to E. Further, the surface—i.e., the surface that comes into contact with hair—of each fiber structure member was provided with a plurality of depressions according to the pattern illustrated in FIG. 7(c). A 6-by-8-cm rectangular liquid-impermeable sheet was prepared, which was constituted by an aluminum-evaporated thermoplastic resin film. The aforementioned fiber structure members were respectively arranged in a central portion of the respective liquid-impermeable sheets, and each fiber structure member and liquid-impermeable sheet were partially joined together by fusion bonding at a plurality of sections separated from one another as illustrated in FIG. 1, to obtain each hair treatment tool.

The nonwoven fabric B shown in Table 1 was manufactured by the wet sheet-forming method as in the nonwoven fabric A. The nonwoven fabrics D and E shown in Table 1 were manufactured according to the spun-lacing method as in the nonwoven fabric C.

TABLE 1

|  |  | Nonwoven fabric A | Nonwoven fabric B | Nonwoven fabric C | Nonwoven fabric D | Nonwoven fabric E |
|---|---|---|---|---|---|---|
| Hydrophilic fiber | Pulp (%) | — | 14 | — | — | — |
|  | Rayon (%) | 22 | 23 | 70 | 70 | 80 |
|  | PVA (%) | 10 | 7 | — | — | — |
| Hydrophobic fiber | PET (%) | 18 | 56 | — | 30 | — |
|  | PP/PE (%) | 50 | — | 30 | — | 20 |
| Hydrophilic fiber (%) |  | 32 | 44 | 70 | 70 | 80 |
| Hydrophobic fiber (%) |  | 68 | 56 | 30 | 30 | 20 |
| Basis weight (g/m²) |  | 45 | 14 | 60 | 60 | 61 |
| Weight per sheet of 3-by-4-cm nonwoven fabric (g) |  | 0.054 | 0.0168 | 0.072 | 0.072 | 0.0732 |

A hair cosmetic (temporary hair colorant) having the composition shown in Table 2 was prepared according to an ordinary process. Then, the temporary hair colorant was dropped onto each fiber structure member of the respective hair treatment tools of Examples 1 to 12, to impregnate each fiber structure member with the temporary hair colorant. The impregnation rate of the fiber structure member in each Example—i.e., the mass of the fiber structure member after impregnation with the temporary hair colorant to the mass of the fiber structure member before impregnation with the temporary hair colorant—was found. The impregnation rate of each Example is shown in Table 4.

For the respective fiber structure member in each Example, the percentage (%) of the mass of the fiber structure member impregnated at the impregnation rate shown in Table 4 to the maximum mass of the fiber structure member after impregnation was found as the impregnation capacity rate. The "maximum mass of the fiber structure member after impregnation" refers to the mass of the fiber structure member impregnated with the maximum amount of temporary hair colorant that the fiber structure member can be impregnated with and retain. The impregnation capacity rate of each Example is shown in Table 4.

TABLE 2

| Composition of hair cosmetic (temporary hair colorant) | Mass % |
|---|---|
| Pigment: Bengara Shippo (iron red) from Miyoshi Kasei Industry Co., Ltd. | 4 |
| N-propionyl polyethyleneimine/methylpolysiloxane copolymer A (*1) | 3.78 |
| N-propionyl polyethyleneimine/methylpolysiloxane copolymer B (*2) | 9.37 |
| N-propionyl polyethyleneimine/methylpolysiloxane copolymer C (*3) | 1.87 |
| Ethanol | Balance |
| Total | 100 |

*1: Organopolysiloxane A of Synthesis Example 1 in JP 2016-056127A
*2: Organopolysiloxane A of Synthesis Example 1 in JP 2009-149597A
*3: Organopolysiloxane B of Synthesis Example 2 in JP 2009-149597A Evaluation Hair Strand:

A 25-cm-long hair strand (tress) weighing 1.0 g was prepared from straight black hair having no history of chemical treatment and taken from a Japanese person. The hair strand was washed with a model shampoo prepared according to the formula of Table 3. The hair strand was then towel dried, and then dried with a hairdryer (Solis Dryer 315 from Solis Ltd.) for 1 minute, and this hair strand was used for evaluation (referred to hereinafter also as "evaluation hair strand").

TABLE 3

| Composition of model shampoo | Mass % |
|---|---|
| Sodium polyoxyethylene (2.5) lauryl ether sulfate | 15.5 |
| Lauric acid diethanolamide | 2.28 |
| Disodium edetate | 0.1 |
| Sodium benzoate | 0.5 |
| Oxybenzone | 0.03 |
| Phosphoric acid | 0.075 |

TABLE 3-continued

| Composition of model shampoo | Mass % |
|---|---|
| Dibutylhydroxytoluene | 0.01 |
| Sodium chloride | 0.8 |
| Food Red No. 106 | 0.00012 |
| Perfume | 0.26 |
| Purified water | Balance |

Evaluation 1:

The respective hair treatment tools of Examples 1 to 4 were each folded in two, and an evaluation hair strand (tress) was sandwiched by the respective folded hair treatment tool at a position 0.5 cm from the bound-side end of the tress. The hair treatment tool was moved toward the other end of the tress in a state where the tress was kept sandwiched by the hair treatment tool, to thereby apply the hair cosmetic (temporary hair colorant) to the tress. The speed of movement of the hair treatment tool upon application was 1.5 cm/second. After application of the hair cosmetic to the tress, the weight of the hair treatment tool was measured, to measure the amount of application of the hair cosmetic to the hair strand (tress). The respective measurement result is shown in Table 4 as "amount of application to hair strand".

The tress was then left at room temperature (25° C.) for 30 seconds to make the tress semi-dry, and then, the tress was combed a total of ten times, once per second, with a comb (HK0103B's Set Comb L from Kai Corporation). Evaluations were made regarding the feel of use upon application, as well as uniform pigment applicability, pigment transfer efficiency, the feel of hair after coloring, and temporal stability of the hair strand after coloring obtained as above, according to each of the following methods and evaluation criteria. The evaluation results are shown in Table 4.

Feel of Use Upon Application:

The feel of use upon sandwiching the hair strand with the hair treatment tool and applying the hair cosmetic to the hair strand was evaluated by five panelists on the following 1-to-4 scale. The total score of the evaluation is shown in Table 4.

4: Liquid is discharged sufficiently upon application, and user feels he/she is being able to perform application.

3: Liquid is discharged somewhat upon application, and user somewhat feels he/she is being able to perform application.

2: Liquid is somewhat hard to discharge upon application, and user somewhat does not feel he/she is being able to perform application.

1: Liquid is not discharged sufficiently upon application, and user does not feel he/she is being able to perform application.

Uniform Pigment Applicability:

The characteristics of applying the pigment uniformly (uniform pigment applicability) was evaluated by visually observing the intensity of coloring from the bound-side one end (upper portion) of the evaluation hair strand to the tip end of the hair (lower portion). Five panelists performed visual evaluation on the following 1-to-4 scale. The total score of the evaluation is shown in Table 4.

4: Coloring is uniform from the upper portion to the lower portion.

3: Coloring is rather uniform from the upper portion to the lower portion.

2: Coloring is rather uneven from the upper portion to the lower portion.

1: Coloring is uneven from the upper portion to the lower portion.

Transfer Efficiency of Pigment to Hair:

For the colored tress, the efficiency of transfer of the pigment to the hair (pigment transfer efficiency) was evaluated by visually observing whether the original black hair was covered and was sufficiently colored. Five panelists performed visual evaluation on the following 1-to-4 scale. The total score of the evaluation is shown in Table 4.

4: Black hair was covered completely, and the hair was clearly colored to a color different from the original hair color.

3: Black hair was covered almost completely, and the hair was colored to a color different from the original hair color.

2: Black hair was somewhat covered, and the hair was somewhat colored to a color different from the original hair color.

1: Black hair was not covered, and the hair was not colored.

Feel of Hair after Coloring:

The feel of the hair (hair strand) after coloring was evaluated by sensory evaluation. Five panelists performed evaluation on the following 1-to-4 scale. The total score of the evaluation is shown in Table 4.

4: Absolutely no roughness or stiffness, and excellent feel to the touch.

3: Almost no roughness or stiffness, and somewhat good feel to the touch.

2: Somewhat rough or stiff, and somewhat poor feel to the touch.

1: Rough and stiff, and poor feel to the touch.

Temporal Stability:

Each of the hair treatment tools of Examples 1 to 13 was folded in two, and the perimeter of the liquid-impermeable sheet was sealed by fusion bonding. Each hair treatment tool was then laid horizontally in a constant-temperature chamber (Tabai constant-temperature high-humidity chamber from Espec Corp.) set to the following conditions, and was stored for six days.

Setting conditions of constant-temperature chamber: The temperature was raised from −15° C. to 60° C. (6.25° C./h), and then lowered from 60° C. to −15° C. (−6.25° C./h), and this temperature cycle was performed over a single day.

After storage for six days, each hair treatment tool was taken out from the constant-temperature chamber and the temperature thereof was adjusted by keeping the tools still at room temperature for 6 hours. Then, evaluation was performed according to the same process/procedure and evaluation criteria as in the aforementioned Uniform Pigment Applicability. The total score of the evaluation is shown in Table 4.

TABLE 4

| | | | Example 1 | Example 2 | Example 3 | Example 4 | Example 5 | Example 6 |
|---|---|---|---|---|---|---|---|---|
| Nonwoven fabric | Nonwoven fabric A | Application layer | 2 sheets | — | 2 sheets | 2 sheets | 4 sheets | 6 sheets |
| | Nonwoven fabric B | | — | 8 sheets | — | — | — | — |

TABLE 4-continued

| | | | | | | | | |
|---|---|---|---|---|---|---|---|---|
| | Nonwoven fabric C | | — | — | — | — | — | — |
| | Nonwoven fabric A | Lower layer | — | — | — | — | — | — |
| | Nonwoven fabric B | | — | — | — | — | — | — |
| | Nonwoven fabric C | | 3 sheets | — | — | 6 sheets | 4 sheets | 2 sheets |
| | Nonwoven fabric D | | — | 2 sheets | — | — | — | — |
| | Nonwoven fabric E | | — | — | 1 sheet | — | — | — |
| Surface layer | | | Nonwoven fabric A | Nonwoven fabric B | Nonwoven fabric A | Nonwoven fabric A | Nonwoven fabric A | Nonwoven fabric A |
| Content by percentage of cellulosic fiber in nonwoven fabric of application layer (%) | | | 22% | 37% | 22% | 22% | 22% | 22% |
| Content by percentage of cellulosic fiber in nonwoven fabric of lower layer (%) | | | 70% | 70% | 80% | 70% | 70% | 70% |
| Impregnation rate | | | 430% | 430% | 430% | 370% | 350% | 340% |
| Impregnation capacity rate | | | 90% | 90% | 90% | 90% | 90% | 90% |
| Amount of application to hair strand | | | 0.42 g | 0.32 g | 0.32 g | 0.38 g | 0.37 g | 0.39 g |
| Evaluation items | Feel of use upon application | | 20 | 16 | 15 | 15 | 16 | 17 |
| | Uniform pigment applicability | | 20 | 19 | 16 | 19 | 19 | 19 |
| | Pigment transfer efficiency | | 19 | 17 | 18 | 18 | 18 | 18 |
| | Feel of hair after coloring | | 19 | 20 | 19 | 19 | 19 | 19 |
| | Temporal stability | | 5 | 6 | 4 | 16 | 15 | 14 |

| | | | Example 7 | Example 8 | Example 9 | Example 10 | Example 11 | Example 12 |
|---|---|---|---|---|---|---|---|---|
| Nonwoven fabric | Nonwoven fabric A | Application layer | 8 sheets | — | — | — | — | 10 sheets |
| | Nonwoven fabric B | | — | — | — | — | — | — |
| | Nonwoven fabric C | | — | 2 sheets | 4 sheets | 6 sheets | 8 sheets | — |
| | Nonwoven fabric A | Lower layer | — | 6 sheets | 4 sheets | 2 sheets | — | — |
| | Nonwoven fabric B | | — | — | — | — | — | — |
| | Nonwoven fabric C | | — | — | — | — | — | — |
| | Nonwoven fabric D | | — | — | — | — | — | — |
| | Nonwoven fabric E | | — | — | — | — | — | — |
| Surface layer | | | Nonwoven fabric A | Nonwoven fabric C | Nonwoven fabric C | Nonwoven fabric C | Nonwoven fabric C | Nonwoven fabric A |
| Content by percentage of cellulosic fiber in nonwoven fabric of application layer (%) | | | 22% | 70% | 70% | 70% | 70% | 22% |
| Content by percentage of cellulosic fiber in nonwoven fabric of lower layer (%) | | | — | 22% | 22% | 22% | — | — |
| Impregnation rate | | | 370% | 340% | 350% | 370% | 380% | 330% |
| Impregnation capacity rate | | | 90% | 90% | 90% | 90% | 90% | 90% |
| Amount of application to hair strand | | | 0.34 g | 0.37 g | 0.33 g | 0.38 g | 0.37 g | 0.40 g |
| Evaluation items | Feel of use upon application | | 18 | 17 | 16 | 15 | 14 | 17 |
| | Uniform pigment applicability | | 19 | 18 | 18 | 18 | 18 | 19 |
| | Pigment transfer efficiency | | 18 | 17 | 17 | 17 | 17 | 17 |
| | Feel of hair after coloring | | 19 | 19 | 19 | 19 | 19 | 19 |
| | Temporal stability | | 14 | 15 | 16 | 18 | 15 | 15 |

The hair treatment tools of Examples 1 to 12 exhibited excellent uniform applicability and transfer efficiency. Further, the hair treatment tools of Examples 1 to 12 had excellent evaluation results in terms of the feel of the hair after coloring, and also had favorable evaluation results in terms of the feel of use upon application. The hair treatment tools of Examples 4 to 12 had excellent evaluation results in terms of temporal stability. Further, in the evaluation of temporal stability, by using the hair treatment tools of Examples 1 to 12, it was possible to apply the temporary hair colorant to the hair strand without soiling the hands.

Evaluation 2:

The hair treatment tool of Example 1 and other cosmetic tools (Comparative Examples 1 to 3) which are generally used upon application of temporary hair colorants and hair dye agents were used to apply the hair cosmetic shown in Table 2 to an evaluation hair strand. The evaluation hair strand used in the aforementioned Examples was used for the evaluation hair strand herein.

Example 13

To the evaluation hair strand (tress), 0.4 g of the hair cosmetic shown in Table 2 was applied by using the hair treatment tool of Example 1. The hair treatment tool of Example 1 was folded in two and the tress was sandwiched therebetween so that the tress contacted the fiber structure member, and the hair treatment tool was moved in this state toward the other end of the tress, to apply the hair cosmetic to the tress. The number of times required to apply 0.4 g of the hair cosmetic was counted as the number of times of operations upon application. The number of times of operations upon application is shown in Table 5.

Comparative Example 1

0.4 g of the hair cosmetic shown in Table 2 was applied with a mascara brush (attachment of Blaune Point-Cover from Kao Corporation). The number of times required to apply 0.4 g of the hair cosmetic was counted as the number of times of operations upon application. The number of times of operations upon application is shown in Table 5.

Comparative Example 2

0.4 g of the hair cosmetic shown in Table 2 was place on the surface of a hair strand, and was spread uniformly using a brush (attachment of Blaune Aroma and Shine Color Cream from Kao Corporation). The number of times required to spread the hair cosmetic was counted as the number of times of operations upon application. The number of times of operations upon application is shown in Table 5.

Comparative Example 3

0.4 g of the hair cosmetic shown in Table 2 was place on the surface of a hair strand, and was spread uniformly using a sponge (puff attached to Sofina Primavista Beautiful Pure Skin Texture Powder Foundation from Kao Corporation). The number of times required to spread the hair cosmetic uniformly was counted as the number of times of operations upon application. The number of times of operations upon application is shown in Table 5.

For each colored hair strand obtained as above, the uniform pigment applicability was evaluated according to the same method as in the aforementioned Examples, and the ease of performing the application operation was evaluated according to the following method and evaluation criteria.

Ease of Application Operation:

Five panelists evaluated the ease of performing the application operation on a 1-to-4 scale. The total score of the evaluation is shown in Table 5.

4: Easy, and can be applied uniformly by himself/herself.
3: Rather easy, and can be applied rather uniformly by himself/herself.
2: Rather difficult, and difficult to apply uniformly by himself/herself.
1: Difficult, and cannot be applied uniformly by himself/herself.

With the hair treatment tool of Example 13, it was possible to apply 0.4 g of the hair cosmetic in one operation. Further, the hair treatment tool of Example 13 had excellent evaluation results in terms of ease of application operation and uniform pigment applicability.

Evaluation 3:

The fiber structure member of the hair treatment tool of the invention was impregnated with a temporary hair colorant having a different composition and was used to apply the colorant to an evaluation hair strand. As in Examples 1 to 12, the feel of use upon application, uniform pigment applicability, pigment transfer efficiency, the feel of hair after coloring, and temporal stability were evaluated according to each of the aforementioned methods and evaluation criteria.

Examples 14 to 19

Hair treatment tools according to Example 10 were prepared. The fiber structure members of the respective hair treatment tools were impregnated with the respective temporary hair colorants shown in Table 6. As in Examples 1 to 12, the respective hair treatment tools were used to apply the respective temporary hair colorants to respective evaluation hair strands, and the feel of use upon application was evaluated according to the aforementioned method and evaluation criteria. Further, for the respective hair strands after coloring, uniform pigment applicability, pigment transfer efficiency, and the feel of hair after coloring were evaluated according to each of the aforementioned methods and evaluation criteria. The evaluation results are shown in Table 6. Table 6 also shows the evaluation results for Example 10. The evaluation hair strand used in the aforementioned Examples was used for the evaluation hair strand herein.

TABLE 5

|  |  | Example 13 | Comparative Example 1 | Comparative Example 2 | Comparative Example 3 |
|---|---|---|---|---|---|
| Type of cosmetic tool |  | Nonwoven fabric | Mascara brush | Brush | Sponge |
| Amount of application to hair strand |  | 0.41 g | 0.40 g | 0.40 g | 0.40 g |
| Number of times of operations upon application (times) |  | 1 | 18 | 15 | 3 |
| Evaluation items | Ease of application | 19 | 11 | 10 | 15 |
|  | Uniform pigment applicability | 20 | 10 | 16 | 13 |

TABLE 6

| Composition of hair cosmetic (temporary hair colorant) | | Example 10 | Example 14 | Example 15 | Example 16 | Example 17 | Example 18 | Example 19 |
|---|---|---|---|---|---|---|---|---|
| Pigment | Pigment: Bengara Shippo (iron red) from Miyoshi Kasei Industry Co., Ltd. | 4 | | 4 | 4 | 4 | 4 | 4 |
| | Pigment: Red 7 (CI 15850) | | 2 | | | | | |
| | Pigment: Mica (CI 77019) | | 1 | | | | | |
| | Pigment: Titanium Dioxide (CI 77891) | | 1 | | | | | |
| Film-forming resin | N-propionylpolyethyleneimine/ methylpolysiloxane copolymer A (*1) | 3.78 | 3.78 | | | | | |
| | N-propionylpolyethyleneimine/ methylpolysiloxane copolymer B (*2) | 9.37 | 9.37 | | | | | |
| | N-propionylpolyethyleneimine/ methylpolysiloxane copolymer C (*3) | 1.87 | 1.87 | | | | | |
| | Vinyl methyl ether/butyl maleate copolymer (*4) | | | 12 | | | | 12 |
| | Alkyl acrylate/diacetone acrylamide copolymer (*5) | | | | 12 | | | |
| | PEG-12 dimethicone (*6) | | | 8 | 8 | | | |
| | Crotonic acid/vinyl (C8-12) isoalkyl esters/VA/ bisvinyldimethicone crosspolymer (*7) | | | | | 10 | | |
| | Acrylates/methoxy PEG-23 methacrylate copolymer (*8) | | | | | 10 | 10 | |
| | Alkyl acrylate/dimethicone copolymer (*9) | | | | | | 10 | |
| | Polysilicone 13 (*10) | | | | | | | 8 |
| | Ethanol | Balance | Balance | Balance | Balance | Balance | Balance | Balance |
| | Total | 100 | 100 | 100 | 100 | 100 | 100 | 100 |
| Evaluation items | Feel of use upon application | 16 | 16 | 16 | 16 | 16 | 16 | 16 |
| | Uniform pigment applicability | 18 | 18 | 17 | 15 | 15 | 16 | 15 |
| | Pigment transfer efficiency | 17 | 16 | 17 | 17 | 17 | 17 | 17 |
| | Feel of hair after coloring | 19 | 19 | 17 | 16 | 16 | 14 | 14 |

(*1): Organopolysiloxane A of Synthesis Example 1 in JP 2016-056127A
(*2): Organopolysiloxane A of Synthesis Example 1 in JP 2009-149597A
(*3): Organopolysiloxane B of Synthesis Example 2 in JP 2009-149597A
(*4): Gantrez ES-425L from ISP
(*5): Plascize L-9540B from GOO Chemical Co., Ltd.
(*6): SH3775M from Dow Corning Toray Co., Ltd.
(*7): BELSIL P1101 from Wacker Asahikasei Silicone Co., Ltd.
(*8): Acrylates/methoxy PEG-23 methacrylate copolymer in JP 2015-13842A
(*9): KP545 from Shin-Etsu Chemical Co., Ltd.
(*10): FZ2222 from Dow Corning Toray Co., Ltd.

The hair treatment tools of Examples 14 to 19 exhibited excellent uniform applicability and transfer efficiency. Further, the hair treatment tools of Examples 14 to 19 had excellent evaluation results in terms of the feel of the hair after coloring.

Evaluation 4 (Example 20):

As Example 20, a test was performed in which hair was colored using the hair treatment tool of the invention and also the hair was curled. The test method is described below.

The hair treatment tool of Example 1 was folded in two, and an evaluation hair strand (tress) was sandwiched by the folded hair treatment tool at a position 0.5 cm from the bound-side end of the tress, so that the tress contacted the fiber structure member. While being kept in this state, the hair treatment tool was moved toward the other end of the tress, to thereby apply the hair cosmetic (temporary hair colorant) to the tress. The temporary hair colorant with which the fiber structure member of this hair treatment tool was impregnated included a pigment and a film-forming resin including N-propionylpolyethyleneimine/methylpolysiloxane copolymers A to C, as shown in Table 2. The speed of movement of the hair treatment tool upon application was 1.5 cm/second. After application of the hair cosmetic to the tress, the weight of the hair treatment tool was measured, to measure the amount of application of the hair cosmetic to the tress. This yielded the same measurement result as in Example 1.

The tress was then left at room temperature (25° C.) for 30 seconds to make the tress semi-dry, and then, the tress was combed a total of ten times, once per second, with a comb (HK0103B's Set Comb L from Kai Corporation). By this operation, the tress changed from a semi-dry state to a dry state.

Then, the tress was wrapped around a hair iron (Model No. PM81 from Tescom & Co., Ltd.) set to a temperature of 180° C. and kept for 10 seconds, and then the hair strand was removed from the hair iron. As a result, the entire hair strand was colored uniformly, and was made curly.

INDUSTRIAL APPLICABILITY

With the hair treatment method and hair treatment tool of the invention, a cosmetic can be applied easily to a desired portion of the hair, and the cosmetic can be applied uniformly to the hair.

The invention claimed is:

1. A hair treatment method for treating hair by using a hair treatment tool comprising a fiber structure member and a liquid-impermeable sheet to which the fiber structure member is fixed, the fiber structure member retaining a hair cosmetic that comprises a pigment and a film-forming resin, the fiber structure member retaining the hair cosmetic that comprises the pigment and the film-forming resin being sealed in a packaging, the method comprising:
   opening the package to expose a surface of the fiber structure member retaining the hair cosmetic that comprises the pigment and the film-forming resin; and
   bringing the fiber structure member retaining the hair cosmetic that comprises the pigment and the film-forming resin, whose surface has been exposed during said opening, into contact with hair, and in this state, moving the fiber structure member retaining the hair cosmetic that comprises the pigment and the film-forming resin in a direction of orientation of the hair, wherein
   the hair cosmetic comprises 70 mass % or greater of an organic solvent having a boiling point of from 50° C. to 260° C., and a content by percentage of water that is 10 mass % or less,
   the hair cosmetic is a temporary hair colorant,
   the fiber structure member has a structure formed by layering a plurality of layers,
   the fiber structure member comprises:
      an application layer comprising a surface layer constituting the surface that contacts the hair, and
      a lower layer arranged more toward the liquid-impermeable sheet side than the application layer;
   each of the application layer and the lower layer is constituted by a single layer or by a layered structure formed by layering a plurality of sheets each having a same impregnation rate of the hair cosmetic and a same content by percentage of cellulosic fiber;
   a content by percentage of cellulosic fiber in all constituent fibers of the application layer is different from a content by percentage of cellulosic fiber in all constituent fibers of the lower layer; and
   a content by percentage of cellulosic fiber in the lower layer with respect to the mass of all constituent fibers in the lower layer is from 60 to 95 mass %; or
   a content by percentage of cellulosic fiber in the application layer with respect to the mass of all constituent fibers in the application layer is from 60 to 95 mass %.

2. The hair treatment method according to claim 1, wherein, in said bringing, the fiber structure member is folded in two in a manner that the surface thereof faces inward, and the fiber structure member is moved in the direction of orientation of the hair in a state where a hair strand is sandwiched between the fiber structure member having been folded in two.

3. The hair treatment method according to claim 1, wherein the hair cosmetic has a viscosity of 2500 mPa·s or less at 30° C.

4. The hair treatment method according to claim 1, wherein the content by percentage of cellulosic fiber in all constituent fibers of the application layer is lower than the content by percentage of cellulosic fiber in all constituent fibers of the lower layer.

5. The hair treatment method according to claim 1, wherein at least a surface side of the surface layer comprises from 5 to 60 mass % of cellulosic fiber.

6. The hair treatment method according to claim 1, wherein an entirety or a portion of the packaging is formed by the liquid-impermeable sheet.

7. The hair treatment method according to claim 1, wherein the fiber structure member is contained in a folded state in the packaging.

8. The hair treatment method according to claim 1, wherein the film-forming resin comprises at least one type of resin selected from the group consisting of cationic resins and anionic resins.

* * * * *